(12) United States Patent
Burak et al.

(10) Patent No.: US 11,446,401 B2
(45) Date of Patent: Sep. 20, 2022

(54) ACTINIUM-225 AND CHECKPOINT INHIBITOR COMBINATION THERAPY

(71) Applicant: Fusion Pharmaceuticals Inc., Hamilton (CA)

(72) Inventors: Eric Steven Burak, Cambridge (CA); Julie Metcalf, Toronto (CA); Natalie Grinshtein, Oakville (CA); Meiduo Hu, Maple (CA); John Fitzmaurice Valliant, Ancaster (CA)

(73) Assignee: Fusion Pharmaceuticals Inc., Hamilton (CA)

( * ) Notice: Subject to any disclaimer, the term of this patent is extended or adjusted under 35 U.S.C. 154(b) by 0 days.

(21) Appl. No.: 16/619,432

(22) PCT Filed: Dec. 3, 2019

(86) PCT No.: PCT/IB2019/001342
§ 371 (c)(1),
(2) Date: Dec. 4, 2019

(87) PCT Pub. No.: WO2020/115556
PCT Pub. Date: Jun. 11, 2020

(65) Prior Publication Data
US 2022/0088230 A1 Mar. 24, 2022

Related U.S. Application Data

(60) Provisional application No. 62/774,847, filed on Dec. 3, 2018.

(51) Int. Cl.
*A61P 37/04* (2006.01)
*A61K 51/10* (2006.01)
*A61P 35/00* (2006.01)
*A61K 31/502* (2006.01)
*A61K 31/5377* (2006.01)
*A61K 45/06* (2006.01)
*A61K 51/04* (2006.01)
*A61K 39/395* (2006.01)
*C07K 16/28* (2006.01)
*A61P 35/04* (2006.01)
*A61K 39/00* (2006.01)

(52) U.S. Cl.
CPC ........ *A61K 51/1036* (2013.01); *A61K 31/502* (2013.01); *A61K 31/5377* (2013.01); *A61K 39/3955* (2013.01); *A61K 45/06* (2013.01); *A61K 51/0482* (2013.01); *A61K 51/103* (2013.01); *A61K 51/1045* (2013.01); *A61K 51/1075* (2013.01); *A61K 51/1093* (2013.01); *A61P 35/00* (2018.01); *A61P 35/04* (2018.01); *A61P 37/04* (2018.01); *C07K 16/28* (2013.01); *C07K 16/2851* (2013.01); *C07K 16/2863* (2013.01); *A61K 2039/505* (2013.01)

(58) Field of Classification Search
None
See application file for complete search history.

(56) References Cited

U.S. PATENT DOCUMENTS

| 6,180,370 | B1 | 1/2001 | Queen et al. | |
|---|---|---|---|---|
| 7,736,651 | B1* | 6/2010 | Scheinberg | A61P 31/00 424/178.1 |
| 2007/0243194 | A1* | 10/2007 | Hariharan | A61P 35/00 536/23.53 |
| 2010/0008906 | A1* | 1/2010 | Glaser | A61P 35/00 435/69.6 |
| 2017/0327567 | A1* | 11/2017 | Skokos | A61K 39/395 |
| 2018/0126012 | A1* | 5/2018 | Weichert | A61K 51/1045 |
| 2019/0160179 | A1 | 5/2019 | Neville et al. | |
| 2019/0192655 | A1 | 6/2019 | Stewart et al. | |
| 2019/0224294 | A1 | 7/2019 | Akle et al. | |

FOREIGN PATENT DOCUMENTS

| WO | WO-1992022324 | A1 | | 12/1992 | | |
|---|---|---|---|---|---|---|
| WO | WO-1998046645 | A2 | | 10/1998 | | |
| WO | WO-2011068845 | A1 | | 6/2011 | | |
| WO | WO2016172249 | | * | 10/2016 | ............. | C07K 14/82 |
| WO | WO2016196377 | | * | 12/2016 | ............. | C07K 16/28 |
| WO | WO-2017123556 | A1 | | 7/2017 | | |
| WO | WO-2017134234 | A1 | | 8/2017 | | |
| WO | WO-2018049474 | A1 | | 3/2018 | | |
| WO | WO2019055706 | | * | 3/2019 | ............. | A61K 51/08 |

OTHER PUBLICATIONS

Beckwith et al., "Minireview: Were the IGF Signaling Inhibitors All Bad?" Mol. Endocrinol. 29(11):1549-1557 (2015).
Beeson et al., "Conditionally Cleavable Radioimmunoconjugates: A Novel Approach for the Release of Radioisotopes from Radioimmunoconjugates," Bioconjug. Chem. 14(5):927-933 (2003).
Berge et al., "Pharmaceutical Salts," J. Pharm. Sci. 66(1):1-19 (1977).
Bockel et al., "Combining Radiation Therapy and Cancer Immune Therapies: From Preclinical Findings to Clinical Applications," Cancer Radiother. 22 (6-7):567-580 (2018).
Brinkman et al., "Phage Display of Disulfide-Stabilized Fv Fragments," J. Immunol. Methods. 182:41-50(1995).
Chappell et al., "Synthesis, Conjugation, and Radiolabeling of a Novel Bifunctional Chelating Agent for (225)Ac Radioimmunotherapy Applications," Bioconjug. Chem. 11(4):510-519 (2000).
Cornelissen et al., "Molecular Radiotherapy Using Cleavable Radioimmunoconjugates that Target EGFR and γH2AX," Mol. Cancer Ther. 12(11):2472-2482 (2013).
Cushman et al., "Combining Radiation Plus Immunotherapy to Improve Systemic Immune Response," J. Thorac. Dis. 10:(Suppl 3):S468-S479 (2018).
Orcutt et al., "Biodistribution and Clearance of Small Molecule Hapten Chelates for Pretargeted Radioimmunotherapy," Mol. Imaging Biol. 13(2):215-221 (2011).

(Continued)

*Primary Examiner* — Elly-Gerald Stoica
(74) *Attorney, Agent, or Firm* — Goodwin Procter LLP

(57) ABSTRACT

Combination therapies comprising administering radioimmunoconjugates and one or more checkpoint inhibitors.

1 Claim, 7 Drawing Sheets
Specification includes a Sequence Listing.

(56) References Cited

OTHER PUBLICATIONS

Derer et al., "Radio-immunotherapy-induced Immunogenic Cancer Cells as Basis for Induction of Systemic Anti-tumor Immune Responses—Pre-clinical Evidence and Ongoing Clinical Applications," Front Immunol. 8(6):505 (2015).
Fusion Pharmaceuticals Inc., "A Phase 1 Study of [225Ac]-FPI-1434 Injection," Nov. 19, 2018, online, retrieved Jul. 22, 2020, retrieved from https://clinicaltrials.gov/ct2/show/NCT03746431.
Gorin et al., "Antitumor Immunity Induced after a Irradiation," Neoplasia 16(4):319-328 (2014).
Greene and Wuts, "Protective Groups in Organic Synthesis," 3rd Edition, John Wiley & Sons, (1999).
Harlow and Lane, "Antibodies: A Laboratory Manual," 1st Edition, Cold Spring Harbor Laboratory Press, pp. 726 (1988).
International Search Report and Written Opinion for International Application No. PCT/IB2019/001342, dated Apr. 28, 2020 (22 pages).
Kumaresan et al., "On-Demand Cleavable Linkers for Radioimmunotherapy," Methods Mol. Biol. 539:191-211 (2009).
Langer, "New Methods of Drug Delivery," Science, 249(4976):1527-1533 (1990).
Li et al., "Vinyl Sulfone Bifunctional Derivatives of DOTA Allow Sulfhydryl or Amino-Directed Coupling to Antibodies. Conjugates Retain Immunoreactivity and Have Similar Biodistributions," Bioconjug. Chem.13(1):110-115 (2002).
Morrison, "Transfectomas Provide Novel Chimeric Antibodies," Science. 229(4719):1202-1207 (2017).
Segal et al., "Introduction: Bispecific Antibodies," J. Immunol. Methods. 248(1-2):1-6 (2001).
Sgouros et al., "MIRD Pamphlet No. 22 (Abridged): Radiobiology and Dosimetry of α-Particle Emitters for Targeted Radionuclide Therapy," J. Nucl. Med. 51(2):311-328 (2010).
Ward et al., "Binding Activities of a Repertoire of Single Immunoglobulin Variable Domains Secreted from *Escherichia coli*," Nature. 341(6242):544-546 (1989).
Cooper et al., "Comparison of (64)Cu-Complexing Bifunctional Chelators for Radioimmunoconjugation: Labeling Efficiency, Specific Activity and In Vitro/In Vivo Stability," Bioconjug. Chem. 23(5):1029-1039 (2012).
Tutt et al., "Trispecific F(ab')3 Derivatives That Use Cooperative Signaling via the TCR/CD3 Complex and CD2 to Activate and Redirect Resting Cytotoxic T Cells," J. Immunol. 147(1):60-69 (1991).
Confino H, Hochman I, Efrati M, Schmidt M, Umansky V, Kelson I, Keisari Y. Tumor ablation by intratumoral Ra-224-loaded wires induces anti-tumor immunity against experimental metastatic tumors. Cancer Immunol Immunother. Feb. 2015;64(2):191-9.
Confino H, Schmidt M, Efrati M, Hochman I, Umansky V, Kelson I, Keisari Y. Inhibition of mouse breast adenocarcinoma growth by ablation with intratumoral alpha-irradiation combined with inhibitors of immunosuppression and CpG. Cancer Immunol Immunother. Oct. 2016;65(10):1149-58.
Demaria S, Ng B, Devitt ML, Babb JS, Kawashima N, Liebes L, Formenti SC. Ionizing radiation inhibition of distant untreated tumors (abscopal effect) is immune mediated. Int J Radiat Oncol Biol Phys. Mar. 1, 2004;58(3):862-70.
Domankevich V, Cohen A, Efrati M, Schmidt M, Rammensee HG, Nair SS, Tewari A, Kelson I, Keisari Y. Combining alpha radiation-based brachytherapy with immunomodulators promotes complete tumor regression in mice via tumor-specific long-term immune response. Cancer Immunol Immunother. Dec. 2019;68(12):1949-1958.
Grass GD. Krishna N, Kim S. The immune mechanisms of abscopal effect in radiation therapy. Curr Probl Cancer. Jan.-Feb. 2016;40(1):10-24.
Grosso J.F, et al., CTLA-4 blockade in tumor models: an overview of preclinical and translational research. Cancer Immun. 2013;13:5.
Kaur et al., A mouse model for triple-negative breast cancer tumor-initiating cells (TNBC-TICs) exhibits similar aggressive phenotype to the human disease, BMC Cancer. Mar. 27, 2012;12:120.
Kim K et al., Eradication of metastatic mouse cancers resistant to immune checkpoint blockade by suppression of myeloid-derived cells. Proc Natl Acad Sci USA. Aug. 12, 2014;111(32):11774-9.
Pulaski B.A. et al., Cooperativity of *Staphylococcal aureus* enterotoxin B superantigen, major histocompatibility complex class II, and CD80 for immunotherapy of advanced spontaneous metastases in a clinically relevant postoperative mouse breast cancer model. Cancer Res, May 15, 2000;60(10):2710-5.

\* cited by examiner

SEQUENCE LISTING

<160> NUMBER OF SEQ ID NOS: 24

<210> SEQ ID NO 1
<211> LENGTH: 16
<212> TYPE: PRT
<213> ORGANISM: Artificial Sequence
<220> FEATURE:
<223> OTHER INFORMATION: CDR-L1 of AVE1642

```
<400> SEQUENCE: 1

Arg Ser Ser Gln Ser Ile Val His Ser Asn Val Asn Thr Tyr Leu Glu
 1               5                  10                  15

<210> SEQ ID NO 2
<211> LENGTH: 7
<212> TYPE: PRT
<213> ORGANISM: Artificial Sequence
<220> FEATURE:
<223> OTHER INFORMATION: CDR-L2 of AVE1642

<400> SEQUENCE: 2

Lys Val Ser Asn Arg Phe Ser
 1               5

<210> SEQ ID NO 3
<211> LENGTH: 9
<212> TYPE: PRT
<213> ORGANISM: Artificial Sequence
<220> FEATURE:
<223> OTHER INFORMATION: CDR-L3 of AVE1642

<400> SEQUENCE: 3

Phe Gln Gly Ser His Val Pro Pro Thr
 1               5

<210> SEQ ID NO 4
<211> LENGTH: 150
<212> TYPE: PRT
<213> ORGANISM: Artificial Sequence
<220> FEATURE:
<223> OTHER INFORMATION: Light chain variable region of AVE1642

<400> SEQUENCE: 4

Asp Val Val Met Thr Gln Thr Pro Leu Ser Leu Pro Val Ser Leu Gly
 1               5                  10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys
145                 150

<210> SEQ ID NO 5
<211> LENGTH: 5
<212> TYPE: PRT
<213> ORGANISM: Artificial Sequence
<220> FEATURE:
<223> OTHER INFORMATION: CDR-H1 of AVE1642
```

```
<400> SEQUENCE: 5

Ser Tyr Trp Met His
1               5

<210> SEQ ID NO 6
<211> LENGTH: 18
<212> TYPE: PRT
<213> ORGANISM: Artificial Sequence
<220> FEATURE:
<223> OTHER INFORMATION: CDR-H2 of AVE1642

<400> SEQUENCE: 6

Gly Glu Ile Asn Pro Ser Asn Gly Arg Thr Asn Tyr Asn Gln Lys Phe
1               5                   10                  15

Gln Gly

<210> SEQ ID NO 7
<211> LENGTH: 15
<212> TYPE: PRT
<213> ORGANISM: Artificial Sequence
<220> FEATURE:
<223> OTHER INFORMATION: CDR-H3 for AVE1642

<400> SEQUENCE: 7

Gly Arg Pro Asp Tyr Tyr Gly Ser Ser Lys Trp Tyr Phe Asp Val
1               5                   10                  15

<210> SEQ ID NO 8
<211> LENGTH: 150
<212> TYPE: PRT
<213> ORGANISM: Artificial Sequence
<220> FEATURE:
<223> OTHER INFORMATION: Heavy chain variable region of AVE1642

<400> SEQUENCE: 8

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly
145                 150

<210> SEQ ID NO 9
<211> LENGTH: 12
<212> TYPE: PRT
<213> ORGANISM: Artificial Sequence
<220> FEATURE:
```

<223> OTHER INFORMATION: Epitope for endosialin antibody

<400> SEQUENCE: 9

Ser Arg Asp His Gln Ile Pro Val Ile Ala Ala Asn
1               5                   10

<210> SEQ ID NO 10
<211> LENGTH: 5
<212> TYPE: PRT
<213> ORGANISM: Artificial Sequence
<220> FEATURE:
<223> OTHER INFORMATION: CDR-H1 for endosialin antibody

<400> SEQUENCE: 10

Gly Tyr Gly Val Asn
1               5

<210> SEQ ID NO 11
<211> LENGTH: 10
<212> TYPE: PRT
<213> ORGANISM: Artificial Sequence
<220> FEATURE:
<223> OTHER INFORMATION: CDR-H1 for endosialin antibody

<400> SEQUENCE: 11

Gly Phe Ser Leu Thr Gly Tyr Gly Val Asn
1               5                   10

<210> SEQ ID NO 12
<211> LENGTH: 16
<212> TYPE: PRT
<213> ORGANISM: Artificial Sequence
<220> FEATURE:
<223> OTHER INFORMATION: CDR-H2 for endosialin antibody

<400> SEQUENCE: 12

Met Ile Trp Val Asp Gly Ser Thr Asp Tyr Asn Ser Ala Leu Lys Ser
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: CDR-H3 for endosialin antibody

<400> SEQUENCE: 13

Gly Gly Tyr Gly Ala Met Asp Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: CDR-L1 for endosialin antibody

<400> SEQUENCE: 14

His Ala Ser Gln Asn Ile Asn Val Trp Leu Thr
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDR-L2 for endosialin antibody

```
<400> SEQUENCE: 15

Lys Ala Ser Asn Leu His Thr
1               5

<210> SEQ ID NO 16
<211> LENGTH: 9
<212> TYPE: PRT
<213> ORGANISM: Artificial Sequence
<220> FEATURE:
<223> OTHER INFORMATION: CDR-L3 for endosialin antibody

<400> SEQUENCE: 16

Gln Gln Gly Gln Ser Tyr Pro Trp Thr
1               5

<210> SEQ ID NO 17
<211> LENGTH: 116
<212> TYPE: PRT
<213> ORGANISM: Artificial Sequence
<220> FEATURE:
<223> OTHER INFORMATION: Humanized VH1 for endosialin antibody

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Thr Ile Ser Val Asp Thr Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Humanized VH2 for endosialin antibody

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Glu Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Asn Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                    85                  90                  95
Arg Gly Gly Tyr Gly Ala Met Asp Tyr Trp Gly Gln Gly Thr Leu Val
                100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Humanized VH3 for endosialin antibody

<400> SEQUENCE: 19

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Thr Ile Ser Val Asp Lys Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
                100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Humanized VH4 for endosialin antibody

<400> SEQUENCE: 20

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Glu Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Asn Ile Ser Val Asp Lys Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
                100                 105                 110

Thr Val Ser Ser
        115

<210> SEQ ID NO 21
<211> LENGTH: 107
```

<212> TYPE: PRT
<213> ORGANISM: Artificial Sequence
<220> FEATURE:
<223> OTHER INFORMATION: Humanized VL1 for endosialin antibody

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Humanized VL2 for endosialin antibody

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Humanized VL3 for endosialin antibody

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Gln Ser Tyr Pro Trp
                 85                  90                  95

Thr Phe Gly Gly Gly Thr Lys Leu Glu Ile Lys
                100                 105

<210> SEQ ID NO 24
<211> LENGTH: 107
<212> TYPE: PRT
<213> ORGANISM: Artificial Sequence
<220> FEATURE:
<223> OTHER INFORMATION: Humanized VL4 for endosialin antibody

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asn Ile Asn Val Trp
                 20                  25                  30

Leu Thr Trp Tyr Gln Gln Lys Pro Glu Lys Ala Pro Lys Ser Leu Ile
             35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Ser Tyr Pro Trp
                 85                  90                  95

Thr Phe Gly Gly Gly Thr Lys Leu Glu Ile Lys
                100                 105
```

ACTINIUM-225 AND CHECKPOINT INHIBITOR COMBINATION THERAPY

CROSS-REFERENCE TO RELATED APPLICATION

The present application is a national stage filing under 35 U.S.C. § 371 of PCT/162019/001342, filed Dec. 3, 2019, which claims the benefit of, and priority to, U.S. Provisional Patent Application No. 62/774,847, filed Dec. 3, 2018, the entire contents of each of which are hereby incorporated by reference for all purposes.

SEQUENCE LISTING

The instant application contains a Sequence Listing which has been submitted electronically in ASCII format via EFS-Web and is hereby incorporated by reference in its entirety. Said ASCII copy, created on Nov. 11, 2021, is named FPI-005WOUS_SL.txt and is 14,830 bytes in size.

BACKGROUND

Cancer cells employ a variety of mechanisms to escape immune surveillance, including suppression of T cell activation.

The mammalian immune system relies on checkpoint molecules to distinguish normal cells from foreign cells. Checkpoint molecules, expressed on certain immune cells, need to be activated or inactivated to start an immune response. Inhibition of checkpoint proteins results in increased activation of the immune system.

Checkpoint inhibition has been explored as a method of immunotherapy for cancer. Inhibiting checkpoint proteins may activate T-cells and allow them to attack cancer cells. However, checkpoint inhibition can allow the immune system to attack some normal cells in the body, which can lead to serious side effects. In addition, some checkpoint inhibitors have exhibited only modest efficacy in the clinic. There remains a need for improved treatments of cancer. In particular, there is a need for increases in efficacy, which do not enhance toxicity in the patient.

SUMMARY

The present disclosure encompasses the insight that combining inhibition of checkpoint proteins with a therapy that targets damage to cancer cells may provide a less toxic therapy with improved efficacy. Radioactive decay can cause direct physical damage (such as single or double-stranded DNA breaks) or indirect damage (such as by-stander or crossfire effects) to the biomolecules that constitute a cell. The present disclosure combines radioimmunoconjugates targeted to cancer cells with checkpoint inhibition to induce or improve an immune response to a tumor. In some embodiments, disclosed combination therapies ameliorate or treat cancer.

In one aspect, provided are methods of inducing an immune response to a tumor in a mammal, said methods comprising: (i) administering to the mammal a radioimmunoconjugate, wherein the mammal has received or is receiving one or more checkpoint inhibitors; (ii) administering to the mammal one or more checkpoint inhibitors, wherein the mammal has received or is receiving a radioimmunoconjugate; or (iii) administering the mammal one or more checkpoint inhibitors at the same time as administering the mammal a radioimmunoconjugate.

In some embodiments, said method comprises administering to a mammal one or more checkpoint inhibitors, wherein the mammal has received or is receiving a radioimmunoconjugate. In some embodiments, the one or more checkpoint inhibitors is administered in a lower effective dose. In some embodiments, the radioimmunoconjugate is administered in a lower effective dose. In some embodiments, both the one or more checkpoint inhibitors and the radioimmunoconjugate are administered in lower effective doses.

In some embodiments, the radioimmunoconjugate comprises (i) a targeting moiety, (ii) a linker, and (iii) a chelating moiety or a metal complex of a chelating moiety.

In some embodiments, the targeting moiety is capable of binding to a tumor-associated antigen. In some embodiments, the tumor-associated antigen is a tumor-specific antigen.

In some embodiments, the targeting moiety is an antibody or an antigen-binding fragment thereof.

In some embodiments, the antibody or antigen-binding fragment thereof is an IGF-1R antibody or an antigen-binding fragment thereof.

In some embodiments, the antibody or antigen-binding fragment thereof is an endosialin (TEM-1) antibody or an antigen-binding fragment thereof.

In some embodiments, the radioimmunoconjugate comprises a metal complex of a chelating moiety. In some embodiments, the metal complex comprises a radionuclide. In some embodiments, the radionuclide is an alpha emitter, e.g., an alpha emitter selected from the group consisting of Astatine-211 ($^{211}$At), Bismuth-212) ($^{212}$Bi), Bismuth-213 ($^{213}$Bi), Actinium-225 ($^{225}$Ac), Radium-223 ($^{223}$Ra), Lead-212 ($^{212}$Pb), Thorium-227 ($^{227}$Th), and Terbium-149 ($^{149}$Tb). In some embodiments, the radionuclide is $^{225}$Ac.

In some embodiments, the radioimmunoconjugate comprises the following structure:

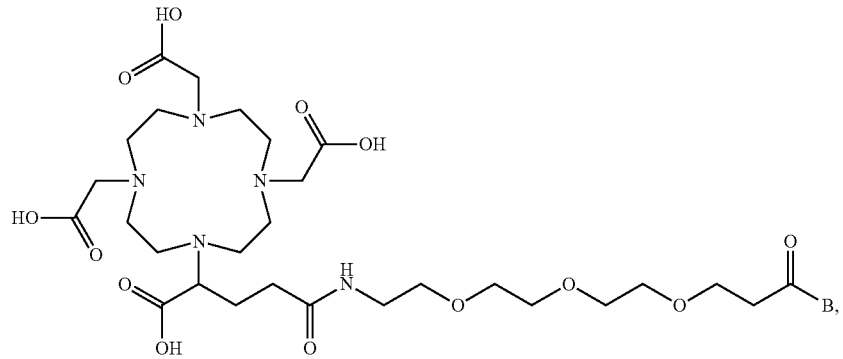

wherein B is the targeting moiety.

In some embodiments, the one or more checkpoint inhibitors comprise a PD-1 inhibitor. In some embodiments, the PD-1 inhibitor is an antibody.

In some embodiments, the one or more checkpoint inhibitors comprise a CTLA-4 inhibitor. In some embodiments, the CTLA-4 inhibitor is an antibody.

In some embodiments, the one or more checkpoint inhibitors comprises both a PD-1 inhibitor and a CTLA-4 inhibitor.

In some embodiments, the mammal is a human.

In some embodiments, the mammal is diagnosed with cancer.

In some embodiments, the cancer is selected from the group comprising: breast cancer, non-small cell lung cancer, small cell lung cancer, pancreatic cancer, head and neck cancer, prostate cancer, colorectal cancer, sarcoma, adrenocortical carcinoma, neuroendocrine cancer, Ewing's Sarcoma, multiple myeloma, or acute myeloid leukemia.

In some embodiments, the mammal has at least one solid tumor.

In some embodiments, said administering results in a therapeutic effect. In some embodiments, said therapeutic effect comprises a decrease in tumor volume, a stable tumor volume, or a reduced rate of increase in tumor volume. In some embodiments, said therapeutic effect comprises a decreased incidence of recurrence or metastasis.

In some embodiments, the targeting moiety is capable of binding to a tumor-associated antigen, and said therapeutic effect comprises an increase in T cells specific for the tumor-associated antigen. In some embodiments, said increase in T cells occurs in the tumor. In some embodiments, said increase in the T cells in the tumor is relative to T cells in the spleen.

In some embodiments, said administering results in at least 15% of the total T cell population in a sample from the mammal being specific for the tumor-associated antigen.

In some embodiments, said administering results in at least 20% of the total T cell population in a sample from the mammal being specific for the tumor-associated antigen.

In some embodiments, said administering results in at least 25% of the total T cell population in a sample from the mammal being specific for the tumor-associated antigen.

In some embodiments, said administering results in at least 30% of the total T cell population in a sample from the mammal being specific for the tumor-associated antigen.

In some embodiments, wherein said administering results in at least 35% of the total T cell population in a sample from the mammal being specific for the tumor-associated antigen.

In some embodiments, said administering results in at least 40% of the total T cell population in a sample from the mammal being specific for the tumor-associated antigen.

In some embodiments, said administering results in at least 45% of the total T cell population in a sample from the mammal being specific for the tumor-associated antigen.

In some embodiments, said administering results in at least 50% of the total T cell population in a sample from the mammal being specific for the tumor-associated antigen.

In some embodiments, said administering results in at least 55% of the total T cell population in a sample from the mammal being specific for the tumor-associated antigen.

In some embodiments, said administering results in at least 60% of the total T cell population in a sample from the mammal being specific for the tumor-associated antigen.

In some embodiments, said administering results in at least 65% of the total T cell population in a sample from the mammal being specific for the tumor-associated antigen.

In some embodiments, said administering results in at least 70% of the total T cell population in a sample from the mammal being specific for the tumor-associated antigen.

In some embodiments, the sample is a tumor sample.

Definitions

Chemical Terms:

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —$C(O)NR^{B'}R^{D'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and $R^{N1}$ is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (19) —NR$^{H'}$C(O)R$^{I'}$, wherein R$^{H'}$ is selected from the group consisting of (a1) hydrogen and (b1) C$_{1-6}$ alkyl, and R$^{I'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (20) —NR$^{J'}$C(O)OR$^{K'}$, wherein R$^{J'}$ is selected from the group consisting of (a1) hydrogen and (b1) C$_{1-6}$ alkyl, and R$^{K'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; and (21) amidine. In some embodiments, each of these groups can be further substituted as described herein. For example, the alkylene group of a C$_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "C$_{x-y}$ alkylene" and the prefix "C$_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., C$_{1-6}$, C$_{1-10}$, C$_{2-20}$, C$_{2-6}$, C$_{2-10}$, or C$_{2-20}$ alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. Amino groups can be unsubstituted amino (i.e., —NH$_2$) or substituted amino (i.e., —N(R$^{N1}$)$_2$) groups. In a preferred embodiment, amino is —NH$_2$ or —NHR$^{N1}$, wherein R$^{N1}$ is, independently, OH, NO$_2$, NH$_2$, NR$^{N2}{}_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, C$_{1-20}$ alkyl (e.g., C$_{1-6}$ alkyl), or C$_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) C$_{1-6}$ alkoxy; (2) C$_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) C$_{6-10}$ aryl-C$_{1-6}$ alkoxy; (5) azido; (6) halo; (7) (C$_{2-9}$ heterocyclyl)oxy; (8) hydroxy; (9) nitro; (10) oxo (e.g., carboxyaldehyde or acyl); (11) C$_{1-7}$ spirocyclyl; (12) thioalkoxy; (13) thiol; (14) —CO$_2$R$^{A'}$, where R$^{A'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) $-C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) $-SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) $-SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) $-C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0to 6, from 1 to 4, from 1 to 6, or from 1 to 10), and R' is H or $C_{1-20}$ alkyl, and (h) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) $-NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) $-NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) $-(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $-(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) $-(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) $-(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclylcan be further substituted with an oxo group to afford the respective aryloyl and (heterocyclyl)oyl substituent group.

The term "arylalkyl," as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "carbonyl," as used herein, represents a C(O) group, which can also be represented as C=O.

The term "carboxy," as used herein, means $-CO_2H$.

The term "cyano," as used herein, represents an $-CN$ group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond or one carbon-carbon triple bond, the cycloalkyl group can be referred to as a "cycloalkenyl" or "cycloalkynyl" group respectively. Exemplary cycloalkenyl and cycloalkynyl groups include cyclopentenyl, cyclohexenyl, cyclohexynyl, and the like. Cycloalkyl groups can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "enantiomer," as used herein, means each individual optically active form of a compound, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halogen," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl(e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (ordiazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

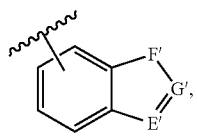

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "hydrocarbon," as used herein, represents a group consisting only of carbon and hydrogen atoms.

The term "hydroxyl," as used herein, represents an OH group. In some embodiments, the hydroxyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound. It is recognized that the compounds can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). Unless otherwise noted, chemical structures depicted herein encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," $^{31d}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, hydroxyl, or carbonyl) group against undesirable reactions during synthetic procedures. Commonly used 0-protecting groups are disclosed in Greene, "Protective Groups in Organic Synthesis," 3$^{rd}$ Edition (John Wiley & Sons, New York, 1999), which is incorporated herein by reference. Exemplary 0-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The term "polyethylene glycol," as used herein, represents an alkoxy chain comprised of one or more monomer units, each monomer unit consisting of —OCH$_2$CH$_2$—. Polyethyelene glycol (PEG) is also sometimes referred to as polyethylene oxide (PEO) or polyoxyethylene (POE), and these terms may be considered interchangeable for the purpose of this disclosure. For example, a polyethylene glycol may have the structure, —(CH$_2$)$_{s2}$(OCH$_2$CH$_2$)$_{s1}$(CH$_2$)$_{s3}$O—, wherein s1 is an integer from 1 to 10 (e.g., from 1 to 6 or from 1 to 4), and each of s2 and s3, independently, is an integer from 0 to 10 (e.g., from 0 to 4, from 0 to 6, from 1 to 4, from 1 to 6, or from 1 to 10). Polyethylene glycol may also be considered to include an amino-polyethylene glycol of —NR$^{N1}$(CH$_2$)$_{s2}$(CH$_2$CH$_2$O)$_{s1}$(CH$_2$)$_{s3}$NR$^{N1}$—, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds may exist in different tautomeric forms, all of the latter being included within the scope of the present disclosure.

The term "sulfonyl," as used herein, represents an —S(O)$_2$— group.

The term "thiol," as used herein represents an —SH group.

Other Terms

As used herein, the term "administered in combination," "combined administration," or "co-administered" means that two or more agents are administered to a subject at the same time or within an interval such that there may be an overlap of an effect of each agent on the patient. Thus, two or more agents that are administered in combination need not be administered together. In some embodiments, they are administered within 90 days (e.g., within 80, 70, 60, 50, 40, 30, 20, 10, 5, 4, 3, 2, or 1 day(s)), within 28 days (e.g., with 14, 7, 6, 5, 4, 3, 2, or 1 day(s), within 24 hours (e.g., 12, 6, 5, 4, 3, 2, or 1 hour(s), or within about 60, 30, 15, 10, 5, or 1 minute of one another. In some embodiments, the administrations of the agents are spaced sufficiently closely together such that a combinatorial effect is achieved.

As used herein, "administering" an agent to a subject includes contacting cells of said subject with the agent.

As used herein, "antibody" refers to a polypeptide whose amino acid sequence including immunoglobulins and fragments thereof which specifically bind to a designated antigen, or fragments thereof. Antibodies may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acid sequences found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains and may include sequence elements found in the same polypeptide chain or in different polypeptide chains.

As used herein, "antigen-binding fragment" refers to a portion of an antibody that retains the binding characteristics of the parent antibody.

The terms "bifunctional chelate" or "bifunctional conjugate" as used interchangeably herein, refer to a compound that contains a chelating group or metal complex thereof, a linker group, and a therapeutic moiety, targeting moiety, or cross-linking group.

The term "cancer" refers to any cancer caused by the proliferation of malignant neoplastic cells, such as tumors, neoplasms, carcinomas, sarcomas, leukemias, and lymphomas. A "solid tumor cancer" is a cancer comprising an abnormal mass of tissue, e.g., sarcomas, carcinomas, and lymphomas. A "hematological cancer" or "liquid cancer," as used interchangeably herein, is a cancer present in a body fluid, e.g., lymphomas and leukemias.

The term "checkpoint inhibitor," also known as "immune checkpoint inhibitor" or "ICI," refers to an agent which blocks the action of an immune checkpoint protein, e.g., blocks such immune checkpoint proteins from binding to their partner proteins.

The term "chelate" as used herein, refers to an organic compound or portion thereof that can be bonded to a central metal or radiometal atom at two or more points.

The term "conjugate," as used herein, refers to a molecule that contains a chelating group or metal complex thereof, a linker group, and which optionally contains a therapeutic moiety, targeting moiety, or cross-linking group.

As used herein, the term "compound," is meant to include all stereoisomers, geometric isomers, and tautomers of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

The term "cross-linking group" as used herein refers to any reactive group that is able to join two or more molecules by a covalent bond. In some embodiments, the cross-linking group is an amino-reactive or thiol-reactive cross-linking group. In some embodiments, the amino-reactive or thiol-reactive cross-linking group comprises an activated ester such as a hydroxysuccinimide ester, 2,3,5,6-tetrafluorophenol ester, 4-nitrophenol ester or an imidate, anhydride, thiol, disulfide, maleimide, azide, alkyne, strained alkyne, strained alkene, halogen, sulfonate, haloacetyl, amine, hydrazide, diazirine, phosphine, tetrazine, isothiocyanate. In some embodiments, the cross-linking group may be glycine-glycine-glycine and/or leucine-proline-(any amino acid)-threonine-glycine, which are the recognition sequences for coupling targeting agents with the linker using a sortase-mediated coupling reaction. The person having ordinary skill in the art will understand that the use of cross-linking groups are not limited to the specific constructs disclosed herein, but rather may include other known cross-linking groups.

As used herein, the terms "decrease," "decreased," "increase," "increased," or "reduction," "reduced," (e.g., in reference to therapeutic outcomes or effects) have meanings relative to a reference level. In some embodiments, the reference level is a level as determined by the use of said method with a control in an experimental animal model or clinical trial. In some embodiments, the reference level is a level in the same subject before or at the beginning of treatment. In some embodiments, the reference level is the average level in a population not being treated by said method of treatment.

As used herein "detection agent" refers to a molecule or atom which is useful in diagnosing a disease by locating the cells containing the antigen. Various methods of labeling polypeptides with detection agents are known in the art. Examples of detection agents include, but are not limited to, radioisotopes and radionuclides, dyes (such as with the biotin-streptavidin complex), contrast agents, luminescent agents (e.g., FITC, rhodamine, lanthanide phosphors, cyanine, and near IR dyes), and magnetic agents, such as gadolinium chelates.

The term an "effective amount" of an agent (e.g., any of the foregoing conjugates), as used herein, is that amount sufficient to effect beneficial or desired results, such as clinical results, and, as such, an "effective amount" depends upon the context in which it is being applied.

The term "immunoconjugate," as used herein, refers to a conjugate that includes a targeting moiety, such as an antibody, nanobody, affibody, or a consensus sequence from Fibronectin type III domain. In some embodiments, the immunoconjugate comprises an average of at least 0.10 conjugates per targeting moiety (e.g., an average of at least 0.2, 0.3, 0.4, 0.5, 0.6, 0.7, 0.8, 0.9, 1, 2, 4, 5, or 8 conjugates per targeting moiety).

The term "lower effective dose," when used as a term in conjunction with an agent (e.g., a therapeutic agent) refers to a dosage of the agent which is effective therapeutically in the combination therapies of the invention and which is lower than the dose which has been determined to be effective therapeutically when the agent is used as a monotherapy in reference experiments or by virtue of other therapeutic guidance.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, radioprotectants, sorbents, suspending or dispersing agents, sweeteners, or waters of hydration. Exemplary excipients include, but are not limited to: ascorbic acid, histidine, phosphate buffer, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts of the compounds described here that are, within the scope of sound medical judgment, suitable for use in contact with the tissues of humans and animals without undue toxicity, irritation, or allergic response. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

Compounds may have ionizable groups so as to be capable of preparation as pharmaceutically acceptable salts. These salts may be acid addition salts involving inorganic or organic acids or the salts may, in the case of acidic forms of compounds, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, among others. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "polypeptide" as used herein refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

The term "radioconjugate," as used herein, refers to any conjugate that includes a radioisotope or radionuclide, such as any of the radioisotopes or radionuclides described herein.

The term "radioimmunoconjugate," as used herein, refers to any immunoconjugate that includes a radioisotope or radionuclide, such as any of the radioisotopes or radionuclides described herein.

The term "radioimmunotherapy," as used herein, refers a method of using a radioimmunoconjugate to produce a therapeutic effect. In some embodiments, radioimmunotherapy may include administration of a radioimmunoconjugate to a subject in need thereof, wherein administration of the radioimmunoconjugate produces a therapeutic effect in the subject. In some embodiments, radioimmunotherapy may include administration of a radioimmunoconjugate to a cell, wherein administration of the radioimmunoconjugate kills the cell. Wherein radioimmunotherapy involves the selective killing of a cell, in some embodiments the cell is a cancer cell in a subject having cancer.

As used herein, the term "radionuclide," refers to an atom capable of undergoing radioactive decay (e.g., $^{3}H$, $^{14}C$, $^{15}N$, $^{18}F$, $^{35}S$, $^{47}Sc$, $^{55}Co$, $^{60}Cu$, $^{61}Cu$, $^{62}Cu$, $^{64}Cu$, $^{67}Cu$, $^{75}Br$, $^{76}Br$, $^{77}Br$, $^{89}Zr$, $^{86}Y$, $^{87}Y$, $^{90}Y$, $^{97}Ru$, $^{99}Tc$, $^{99m}Tc$, $^{105}Rh$, $^{109}Pd$, $^{111}In$, $^{123}I$, $^{124}I$, $^{125}I$, $^{131}I$, $^{149}Pm$, $^{149}Tb$, $^{153}Sm$, $^{166}Ho$, $^{177}Lu$, $^{186}Re$, $^{188}Re$, $^{198}Au$, $^{199}Au$, $^{203}Pb$, $^{211}At$, $^{212}Pb$, $^{212}Bi$, $^{213}Bi$, $^{223}Ra$, $^{225}Ac$, $^{227}Th$, $^{229}Th$, $^{66}Ga$, $^{67}Ga$, $^{68}Ga$, $^{82}Rb$, $^{117m}Sn$, $^{201}Tl$). The terms radioactive nuclide, radioisotope, or radioactive isotope may also be used to describe a radionuclide. Radionuclides may be used as detection agents, as described above. In some embodiments, the radionuclide is an alpha-emitting radionuclide.

By "subject" is meant a human or non-human animal (e.g., a mammal).

By "substantial identity" or "substantially identical" is meant a polypeptide sequence that has the same polypeptide sequence, respectively, as a reference sequence, or has a specified percentage of amino acid residues, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). Sequence identity may be measured using sequence analysis software, e.g., on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

The term "targeting moiety" as used herein refers to any molecule or any part of a molecule that binds to a given target. In some embodiments, the targeting moiety is a protein or polypeptide such as an antibody or antigen binding fragment thereof, a nanobody, an affibody, or a consensus sequence from a Fibronectin type III domain.

The term "therapeutic moiety" as used herein refers to any molecule or any part of a molecule that confers a therapeutic benefit. In some embodiments, the therapeutic moiety is a protein or polypeptide, e.g., an antibody, an antigen-binding fragment thereof. In some embodiments, the therapeutic moiety is a small molecule.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. In the context of cancer treatment, "ameliorating" may include, for example, reducing incidence of metastases, reducing tumor volume, reducing tumor vascularization and/or reducing the rate of tumor growth. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, the term "tumor-associated antigen" means an antigen that is present on tumor cells at a significantly greater amount than on normal cells.

As used herein, the term "tumor-specific antigen" refers to an antigen that is endogenously present only on tumor cells.

Figure 1:
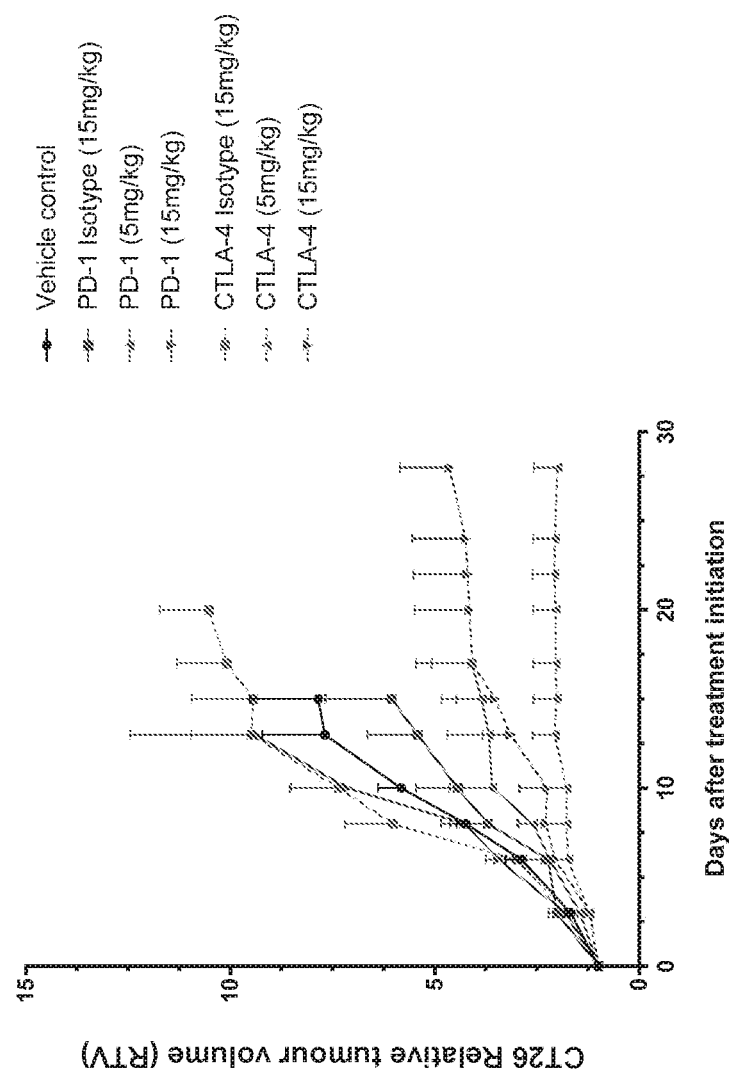
FIG. 1 illustrates relative tumor volume in the CT26 syngeneic mouse tumor model after treatment with various checkpoint inhibitors.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The present disclosure relates to combination therapies for inducing or improving an immune response to cancer using radioimmunoconjugates and checkpoint inhibitors. In some embodiments, use of methods disclosed herein results in treatment or amelioration of cancer.

In some embodiments, a lower effective dose of the radioimmunoconjugate and/or of the checkpoint inhibitor is used.

Radiolabelled targeting moieties (also known as radioimmunoconjugates) are designed to target a protein or receptor that is upregulated in a disease state and/or specific to diseased cells (e.g., tumor cells) to deliver a radioactive payload to damage and kill cells of interest. "Radioimmunotherapy" refers to this therapy when the targeting moiety comprises an antibody, typically a monoclonal antibody. Radioactive decay of the payload produces an alpha, beta, or gamma particle or Auger electron that can cause direct effects to DNA (such as single or double stranded DNA breaks) or indirect effects such as by-stander or crossfire effects.

Radioimmunoconjugates typically contain a biological targeting moiety (e.g., an antibody or antigen binding fragment thereof that specifically binds to a molecule expressed on or by a tumor, e.g., IGF-1R or TEM-1/endosialin), a chelating moiety or a metal complex of a chelating moiety (e.g., comprising a radioisotope), and a linker. Conjugates may be formed by appending a bifunctional chelate to the biological targeting molecule so that structural alterations are minimal while maintaining target affinity. A radioimmunoconjugate may be formed by radiolabelling such a conjugate.

Bifunctional chelates structurally contain a chelate, a linker, and a cross-linking group. When developing new bifunctional chelates, most efforts focus around the chelating portion of the molecule. Several examples of bifunctional chelates have been described with various cyclic and acyclic structures conjugated to a targeted moiety. [Bioconjugate Chem. 2000, 11, 510-519, Bioconjugate Chem. 2012, 23, 1029-1039, Mol Imaging Biol (2011) 13:215-221, Bioconjugate Chem. 2002, 13, 110-115].

Radioimmunoconjugates

Radioimmunoconjugates suitable for use in accordance with the present disclosure generally have the structure of Formula I-a:

A-L-B    Formula I-a wherein A is a chelating moiety or metal complex thereof), wherein B is a targeting moiety, and wherein L is a linker.

In some embodiments, the radioimmunoconjugate comprises the following structure:

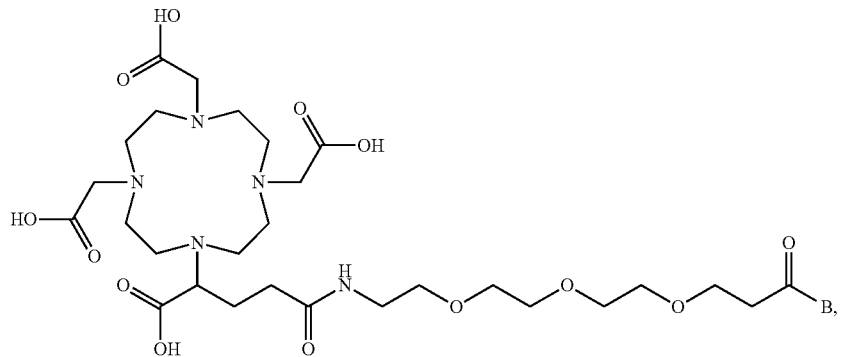

wherein B is the targeting moiety.

Targeting Moieties

Targeting moieties include any molecule or any part of a molecule that is capable of binding to a given target. In some embodiments, the targeting moiety comprises a protein or polypeptide. In some embodiments, the targeting moiety is selected from the group consisting of antibodies or antigen binding fragments thereof, nanobodies, affibodies, and consensus sequences from Fibronectin type III domains (e.g., Centyrins or Adnectins). In some embodiments, a moiety is both a targeting and a therapeutic moiety, i.e., the moiety is capable of binding to a given target and also confers a therapeutic benefit.

Antibodies

Antibodies typically comprise two identical light polypeptide chains and two identical heavy polypeptide chains linked together by disulfide bonds. The first domain located at the amino terminus of each chain is variable in amino acid sequence, providing the antibody-binding specificities of each individual antibody. These are known as variable heavy (VH) and variable light (VL) regions. The other domains of each chain are relatively invariant in amino acid sequence and are known as constant heavy (CH) and constant light (CL) regions. Light chains typically comprise one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelid antibodies, chimeric antibodies, single-chain Fvs (scFv), disulfide-linked Fvs (sdFv), and anti-idiotypic (anti-Id) antibodies, and antigen-binding fragments of any of the above. In some embodiments, the antibody or antigen-binding fragment thereof is humanized. In some embodiments, the antibody or antigen-binding fragment thereof is chimeric. Antibodies can be of any type (e.g., IgG, IgE, IgM, IgD, IgA and IgY), class (e.g., IgG1, IgG2, IgG3, IgG4, IgA1 and IgA2) or subclass.

The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). In some embodiments, an "antigen binding fragment" comprises a heavy chain variable region and a light chain variable region. These antibody fragments can be obtained using conventional techniques known to those with skill in the art, and the fragments can be screened for utility in the same manner as are intact antibodies.

Antibodies or fragments described herein can be produced by any method known in the art for the synthesis of antibodies (see, e.g., Harlow et al., Antibodies: A Laboratory Manual, (Cold Spring Harbor Laboratory Press, 2nd ed.

1988); Brinkman et al., 1995, J. Immunol. Methods 182:41-50; WO 92/22324; WO 98/46645). Chimeric antibodies can be produced using the methods described in, e.g., Morrison, 1985, Science 229:1202, and humanized antibodies by methods described in, e.g., U.S. Pat. No. 6,180,370.

Additional antibodies described herein are bispecific antibodies and multivalent antibodies, as described in, e.g., Segal et al., J. Immunol. Methods 248:1-6 (2001); and Tutt et al., J. Immunol. 147: 60 (1991).

Insulin-Like Growth Factor 1 (IGF-1R) Antibodies

Insulin-like growth factor 1 receptor is a transmembrane protein found on the surface of human cells activated by insulin-like growth factor 1 (IGF-1) and 2 (IGF-2). In some embodiments, radioimmunoconjugates comprise antibodies against insulin-like growth factor-1 receptor (IGF-1R). Although not a typical oncogene, IGF-1R promotes initiation and progression of cancer, playing a critical role in mitogenic transformation and maintenance of the transformed phenotype. IGF-1R has been associated with development of multiple common cancers including breast, lung (e.g., non-small lung), liver, prostate, pancreas, ovarian, colon, melanoma, adrenocortical carcinoma, and various types of sarcomas. IGF-1R signaling stimulates tumour cell proliferation and metabolism, supports angiogenesis, and confers protection from apoptosis. It affects metastatic factors (e.g., HIF-1 dependent hypoxia signaling), anchorage independent growth, as well as growth and survival of tumour metastases after extravasation. IGF-1R has also been implicated in the development, maintenance and enrichment of therapeutic resistant cancer stem cell populations.

Despite the abundance of data implicating IGF-1R's role in cancer, therapeutics targeting IGF-1R have yet to demonstrate a significant impact on disease. There has been much speculation for this lack of efficacy including the inability to identify appropriate biomarkers for patient identification, complexity and interdependency of the IGF-1/IR signaling pathway and the development of other growth hormone compensatory mechanisms [Beckwith and Yee, Mol Endocrinol, November 2015, 29(11):1549-1557]. Radioimmunotherapy, however, may provide a viable mechanism for treating cancers overexpressing the IGF-1 receptor by utilizing the ability of IGF-1R to undergo antibody triggered internalization and lysosomal degradation to deliver targeted radioisotopes inside cancer cells. Internalization and lysosomal degradation of an IGF-1R targeted radioimmunoconjugate prolongs the residence time of the delivered radioisotope inside cancer cells, thereby maximizing the potential for a cell killing emission to occur. In the case of actinium-225, which yields 4 alpha particles per decay chain, cell death can be accomplished by as little as 1 atom of radionuclide delivered per cell [Sgouros, et al. J Nucl Med. 2010, 51:311-2]. Cell killing due to direct DNA impact and breakage by an alpha particle may occur in the targeted cell or in a radius of 2 or 3 non-targeted cells for a given alpha particle decay. In addition to having very high potential anti-tumour potency, IGF-1R targeted radioimmunoconjugates may not generate mechanistic resistance as they do not rely on blocking ligand binding to the receptor to inhibit the oncologic process, as needed with a therapeutic antibody.

Several IGF-1R antibodies have been developed and investigated for the treatment of various types of cancers, including figitumumab, cixutumumab, ganitumab, AVE1642 (also known as humanized EM164 and huEM164), BIIB002, robatumumab, and teprotumumab. After binding to IGF-1R, these antibodies are internalized into the cell and degraded by lysosomal enzymes. The combination of overexpression on tumor cells and internalization offers the possibility of delivering detection agents directly to the tumor site while limiting the exposure of normal tissues to toxic agents.

The CDRs of the light chain variable region of AVE1642 have the sequences:

```
(CDR-L1)
                                              SEQ ID NO: 1
RSSQSIVHSNVNTYLE (CDR-L2)
                                              SEQ ID NO: 2
KVSNRFS (CDR-L3)
                                              SEQ ID NO: 3
FQGSHVPPT
```

The light chain variable region of AVE1642 has the sequence:
SEQ ID NO: 4

```
DVVMTQTPLSLPVSLGDPASISCRSSQSIVHSNVNTYLEWYLQKPGQSPRL

LIYKVSNRFSGVPDRFSGSGAGTDFTLRISRVEAEDLGIYYCFQGSHVPPT

FGGGTKLEIKRTVAAPSVFIFPPSDEQLKSGTASVVCLLNNFYPREAK
```

The CDRs of the heavy chain variable region of AVE1642 have the sequences:

```
(CDR-H1)
                                              SEQ ID NO: 5
SYWMH (CDR-H2)
                                              SEQ ID NO: 6
GEINPSNGRTNY NQKFQG (CDR-H3)
                                              SEQ ID NO: 7
GRPDYYGSSKWY FDV
```

The heavy chain variable region of AVE1642 has the sequence:
SEQ ID NO: 8

```
QVQLVQSGAEVVKPGASVKLSCKASGYTFTSYWMHWVKQRPGQGLEWIGEI

NPSNGRTNYNQKFQGKATLTVDKSSSTAYMQLSSLTSEDSAVYYFARGRPD

YYGSSKWYFDVWGQGTTVTVSSASTKGPSVFPLAPSSKSTSGGTAALG
```

Endosialin (TEM-1) Antibodies

Endosialin, also known as TEM-1 or CD-248, is an antigen expressed by tumor-associated endothelial cells, stromal cells, and pericytes.

Examples of endosialin antibodies include hMP-E-8.3 (disclosed in WO 2017/134234, the entire contents of which are incorporated by reference herein) and ontuxizumab (MORAb-004).

In some embodiments, the endosialin antibody or antigen-binding fragment thereof recognizes an epitope having an amino acid sequence of SRDHQIPVIAAN (SEQ ID NO: 9).

In some embodiments, the heavy chain variable region of the endosialin antibody or antibody-binding fragment thereof comprises the complementarity determining regions (CDRs) having the following sequences:

```
CDR-H1:
                                    (SEQ ID NO: 10)
GYGVN
or
                                    (SEQ ID NO: 11)
GFSLTGYGVN

CDR-H2:
                                    (SEQ ID NO: 12)
MIWVDGSTDYNSALKS

CDR-H3:
                                    (SEQ ID NO: 13)
GGYGAMDY
```

In some embodiments, the light chain variable region of the endosialin antibody or antibody-binding fragment thereof comprises the complementarity determining regions (CDRs) having the following sequences:

```
CDR-L1:
                                    (SEQ ID NO: 14)
HASQNINVWLT

CDR-L2:
                                    (SEQ ID NO: 15)
KASNLHT

CDR-L3:
                                    (SEQ ID NO: 16)
QQGQSYPWT
```

In some embodiments, the endosialin antibody or antigen-binding fragment thereof is a humanized antibody.

In some embodiments, the heavy chain variable region of the endosialin antibody or antigen-binding fragment thereof comprises an amino acid sequence selected from the group consisting of SEQ ID NO: 17, 18, 19, or 20:

```
Humanized VH1:
                                    (SEQ ID NO: 17)
QVQLQESGPGLVKPSETLSLTCTVSGFSLTGYGVNWIRQPPGKGLEWIGMI

WVDGSTDYNSALKSRVTISVDTSKNQFSLKLSSVTAADTAVYYCARGGYGA

MDYWGQGTLVTVSS

Humanized VH2:
                                    (SEQ ID NO: 18)
QVQLQESGPGLVKPSETLSLTCTVSGFSLTGYGVNWIRQPPEKGLEWIGMI

WVDGSTDYNSALKSRVNISVDTSKNQFSLKLSSVTAADTAVYYCARGGYGA

MDYWGQGTLVTVSS

Humanized VH3:
                                    (SEQ ID NO: 19)
QLQLQESGPGLVKPSETLSLTCTVSGFSLTGYGVNWIRQPPGKGLEWIGMI

WVDGSTDYNSALKSRVTISVDKSKNQFSLKLSSVTAADTAVYYCARGGYGA

MDYWGQGTLVTVSS

Humanized VH4:
                                    (SEQ ID NO: 20)
QLQLQESGPGLVKPSETLSLTCTVSGFSLTGYGVNWIRQPPEKGLEWIGMI

WVDGSTDYNSALKSRVNISVDKSKNQFSLKLSSVTAADTAVYYCARGGYGA

MDYWGQGTLVTVSS
```

In some embodiments, the light chain variable region of the endosialin antibody or antigen-binding fragment thereof comprises an amino acid sequence selected from the group consisting of SEQ ID NO: 21, 22, 23, or 24:

```
Humanized VL1:
                                    (SEQ ID NO: 21)
DIQMTQSPSSVSASVGDRVTITCHASQNINVWLTWYQQKPGKAPKLLIYKA

SNLHTGVPSRFSGSGSGTDFTLTISSLQPEDFATYYCQQGQSYPWTFGGGT

KLEIK

Humanized VL2:
                                    (SEQ ID NO: 22)
DIQMTQSPSTLSASVGDRVTITCHASQNINVWLTWYQQKPGKAPKWYKASN

LHTGVPSRFSGSGSGTEFTLTISSLQPDDFATYYCQQGQSYPWTFGGGTKL

EIK

Humanized VL3:
                                    (SEQ ID NO: 23)
DIQMTQSPSSLSASVGDRVTITCHASQNINVWLTWYQQKPGKAPKWYKASN

LHTGVPSRFSGSGSGTDFTFTISSLQPEDIATYYCQQGQSYPWTFGGGTKL

EIK

Humanized VL4:
                                    (SEQ ID NO: 24)
DIQMTQSPSSLSASVGDRVTITCHASQNINVWLTWYQQKPEKAPKSLIYKA

SNLHTGVPSRFSGSGSGTDFTLTISSLQPEDFATYYCQQGQSYPWTFGGGT

KLEIK
```

Nanobodies

Nanobodies are antibody fragments consisting of a single monomeric variable antibody domain. Nanobodies may also be referred to as single-domain antibodies. Like antibodies, nanobodies bind selectively to a specific antigen. Nanobodies may be heavy-chain variable domains or light chain domains. Nanobodies may occur naturally or be the product of biological engineering. Nanobodies may be biologically engineered by site-directed mutagenesis or mutagenic screening (e.g., phage display, yeast display, bacterial display, mRNA display, ribosome display).

Affibodies

Affibodies are polypeptides or proteins engineered to bind to a specific antigen. As such, affibodies may be considered to mimic certain functions of antibodies. Affibodies may be engineered variants of the B-domain in the immunoglobulin-binding region of staphylococcal protein A. Affibodies may be engineered variants of the Z-domain, a B-domain that has lower affinity for the Fab region. Affibodies may be biologically engineered by site-directed mutagenesis or mutagenic screening (e.g., phage display, yeast display, bacterial display, mRNA display, ribosome display).

Affibody molecules showing specific binding to a variety of different proteins (e.g. insulin, fibrinogen, transferrin, tumor necrosis factor-α, IL-8, gp120, CD28, human serum albumin, IgA, IgE, IgM, HER2 and EGFR) have been generated, demonstrating affinities ($K_d$) in the μM to pM range.

Fibronectin Type III Domains

The Fibronectin type III domain is an evolutionarily conserved protein domain found in a wide-variety of extracellular proteins. The Fibronectin type III domain has been used as a molecular scaffold to produce molecules capable of selectively binding a specific antigen. Variants of the Fibronectin type III domains (FN3) that have been engineered for selective-binding may also be referred to as monobodies. FN3 domains may be biologically engineered by site-directed mutagenesis or mutagenic screening (e.g., CIS-display, phage display, yeast display, bacterial display, mRNA display, ribosome display).

Modified Polypeptides

Polypeptides used in accordance with the disclosure may have a modified amino acid sequence. Modified polypeptides may be substantially identical to the corresponding reference polypeptide (e.g., the amino acid sequence of the modified polypeptide may have at least 50%, 60%, 70%, 75%, 80%, 85%, 90%, 95%, 96%, 97%, 98%, 99%, or 100% identity to the amino acid sequence of the reference polypeptide). In certain embodiments, the modification does not destroy significantly a desired biological activity (e.g., binding to IGF-1R or to endosialin). The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified polypeptide may have or may optimize a characteristic of a polypeptide, such as in vivo stability, bioavailability, toxicity, immunological activity, immunological identity, and conjugation properties.

Modifications include those by natural processes, such as post-translational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitinations, and they may be cyclic, with or without branching. Cyclic, branched, and branched cyclic polypeptides may result from post-translational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy-terminus of a polypeptide can facilitate conjugation of these polypeptides by, e.g., disulfide bonding. For example, a polypeptide can be modified to include a single cysteine residue at the amino-terminus or a single cysteine residue at the carboxy-terminus. Amino acid substitutions can be conservative (i.e., wherein a residue is replaced by another of the same general type or group) or non-conservative (i.e., wherein a residue is replaced by an amino acid of another type). In addition, a naturally occurring amino acid can be substituted for a non-naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, N-protected amino acids, an amino acid having an acetylaminomethyl group attached to a sulfur atom of a cysteine, a pegylated amino acid, the omega amino acids of the formula $NH_2(CH_2)_n COOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

TABLE 1

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Chelating Moieties and Metal Complexes Thereof

Chelating Moieties

Examples of suitable chelating moieties include, but are not limited to, DOTA (1,4,7,10-tetraazacyclododecane-1,4,7,10-tetraacetic acid), DOTMA (1R,4R,7R,10R)-α, α', α", α'"-tetramethyl-1,4,7,10-tetraazacyclododecane-1,4,7,10-tetraacetic acid, DOTAM (1,4,7,10-tetrakis(carbamoylmethyl)-1,4,7,10-tetraazacyclododecane), DOTPA (1,4,7,10-tetraazacyclododecane-1,4,7,10-tetra propionic acid), DO3AM-acetic acid (2-(4,7,10-tris(2-amino-2-oxoethyl)-1,4,7,10-tetraazacyclododecan-1-yl)acetic acid), DOTA-GA anhydride (2,2',2''-(10-(2,6-dioxotetrahydro-2H-pyran-3-yl)-1,4,7,10-tetraazacyclododecane-1,4,7-triyl)triacetic acid, DOTP (1,4,7,10-tetraazacyclododecane-1,4,7,10-tetra (methylene phosphonic acid)), DOTMP (1,4,6,10-tetraazacyclodecane-1,4,7,10-tetramethylene phosphonic acid, DOTA-4AMP (1,4,7,10-tetraazacyclododecane-1,4,7,10-tetrakis(acetamido-methylenephosphonic acid), CB-TE2A (1,4,8,11-tetraazabicyclo[6.6.2]hexadecane-4,11-diacetic acid), NOTA (1,4,7-triazacyclononane-1,4,7-triacetic acid), NOTP (1,4,7-triazacyclononane-1,4,7-tri(methylene phosphonic acid), TETPA (1,4,8,11-tetraazacyclotetradecane-1,4,8,11-tetrapropionic acid), TETA (1,4,8,11-tetraazacyclotetradecane-1,4,8,11-tetra acetic acid), HEHA (1,4,7,10,13,16-hexaazacyclohexadecane-1,4,7,10,13,16-hexaacetic acid), PEPA (1,4,7,10,13-pentaazacyclopentadecane-N,N', N'',N''', N''''-pentaacetic acid), Haoctapa (N,N'-bis(6-carboxy-2-pyridylmethyl)-ethylenediamine-N,N'-diacetic acid), H$_2$dedpa (1,2-[[6-(carboxy)-pyridin-2-yl]-methyl-amino]ethane), H$_6$phospa (N,N'-(methylenephosphonate)-N,N'-[6-(methoxycarbonyl)pyridin-2-yl]-methyl-1,2-diaminoethane), TTHA (triethylenetetramine-N,N,N',N'',N''',N''''-hexaacetic acid), DO2P (tetraazacyclododecane dimethanephosphonic acid), HP-DO3A (hydroxypropyltetraazacyclododecanetriacetic acid), EDTA (ethylenediaminetetraacetic acid), Deferoxamine, DTPA (diethylenetriaminepentaacetic acid), DTPA-BMA (diethylenetriaminepentaacetic acid-bismethylamide), HOPO (octadentate hydroxypyridinones), or porphyrins.

In some embodiments, radioimmunoconjugates comprise a metal complex of a chelating moiety. For example, chelating groups may be used in metal chelate combinations with metals, such as manganese, iron, and gadolinium and isotopes (e.g., isotopes in the general energy range of 60 to 4,000 keV), such as any of the radioisotopes and radionuclides discussed herein.[2, 2 2], In some embodiments, chelating moieties are useful as detection agents, and radioimmunoconjugates comprising such detectable chelating moieties can therefore be used as diagnostic or theranostic agents.

Radioisotopes and Radionuclides

In some embodiments, the metal complex comprises a radionuclide. Examples of suitable radioisotopes and radionuclides include, but are not limited to, $^3$H, $^{14}$C, $^{15}$N, $^{18}$F, $^{35}$S, $^{47}$Sc, $^{55}$Co, $^{60}$Cu, $^{61}$Cu, $^{62}$Cu, $^{64}$Cu, $^{66}$Ga, $^{67}$Cu, $^{68}$Ga, $^{75}$Br, $^{76}$Br, $^{77}$Br, $^{82}$Rb, $^{89}$Zr, $^{86}$Y, $^{87}$Y, $^{90}$Y, $^{97}$Ru, $^{99}$Tc, $^{99m}$Tc, $^{105}$Rh, $^{109}$Pd, $^{111}$In, $^{123}$I, $^{124}$I, $^{125}$I, $^{131}$I, $^{149}$Pm, $^{149}$Tb, $^{153}$Sm, $^{166}$Ho, $^{177}$Lu, $^{117m}$Sn, $^{186}$Re, $^{188}$Re, $^{198}$Au, $^{199}$Au, $^{201}$Tl, $^{203}$Pb, $^{211}$At, $^{212}$Pb, $^{212}$Bi, $^{213}$Bi, $^{223}$Ra, $^{225}$Ac, $^{227}$Th, and $^{229}$Th In some embodiments, the radionuclide is an alpha emitter, e.g., Astatine-211 ($^{211}$At), Bismuth-212 ($^{212}$Bi), Bismuth-213 ($^{213}$Bi), Actinium-225 ($^{225}$Ac), Radium-223 ($^{223}$Ra), Lead-212 ($^{212}$Pb), Thorium-227 ($^{227}$Th), or Terbium-149 ($^{149}$Tb).

Linkers

In some embodiments, the linker is as shown within the structure of Formula I-b, as that part of Formula I-b absent A and B:

A-L$^1$-(L$^2$)$_n$-B                                  Formula I-b (A and B are as defined in Formula I-a.)

Thus, in some embodiments, the linker is -L$^1$-(L$^2$)$_n$-,
  wherein L$^1$ is optionally substituted C$_1$-C$_6$ alkyl, substituted C$_1$-C$_6$ heteroalkyl, substituted aryl or heteroaryl; n is 1-5; and
  each L$^2$, independently, has the structure:

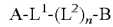                                Formula II wherein is X$^1$ is C=O(NR$^1$), C=S(NR$^1$), OC=O(NR$^1$), NR$^1$C=O(O), NR$^1$C=O(NR$^1$), —CH$_2$PhC=O(NR$^1$), —CH$_2$Ph(NH)C=S(NR$^1$), O, or NR$^1$; and each R$^1$ independently is H or optionally substituted C$_1$-C$_6$ alkyl or optionally substituted C$_1$-C$_6$ heteroalkyl, substituted aryl or heteroaryl, in which C$_1$-C$_6$ alkyl can be substituted by oxo (=O), heteroaryl, or a combination thereof;

L$^3$ is optionally substituted C$_1$-C$_{50}$ alkyl or optionally substituted C$_1$-C$_{50}$ heteroalkyl or C$_5$-C$_{20}$ polyethylene glycol;

Z$^1$ is CH$_2$, C=O, C=S, OC=O, NR$^1$C=O, NR$^1$ and R$^1$ is a hydrogen or optionally substituted C$_1$-C$_6$ alkyl, pyrrolidine-2,5-dione.

Cross-Linking Groups

In some embodiments, radioimmunoconjugates comprise a cross-linking group instead of or in addition to the targeting moiety or therapeutic moiety (e.g., B in Formula I comprises a cross-linking group).

A cross-linking group is a reactive group that is able to join two or more molecules by a covalent bond. Cross-linking groups may be used to attach the linker and chelating moiety to a therapeutic or targeting moiety. Cross-linking groups may also be used to attach the linker and chelating moiety to a target in vivo. In some embodiments, the cross-linking group is an amino-reactive, methionine reactive or thiol-reactive cross-linking group, or a sortase-mediated coupling. In some embodiments, the amino-reactive or thiol-reactive cross-linking group comprises an activated ester such as a hydroxysuccinimide ester, 2,3,5,6-tetrafluorophenol ester, 4-nitrophenol ester or an imidate, anhydride, thiol, disulfide, maleimide, azide, alkyne, strained alkyne, strained alkene, halogen, sulfonate, haloacetyl, amine, hydrazide, diazirine, phosphine, tetrazine, isothiocyanate, or oxaziridine. In some embodiments, the sortase recognition sequence may comprise of a terminal glycine-glycine-glycine (GGG) and/or LPTXG amino acid sequence, where X is any amino acid. A person having ordinary skill in the art will understand that the use of cross-linking groups is not limited to the specific constructs disclosed herein, but rather may include other known cross-linking groups.

Checkpoint Inhibitors

In some embodiments, a checkpoint inhibitor is co-administered with a radioimmunoconjugate.

Generally, suitable checkpoint inhibitors inhibit an immune suppressive checkpoint protein. In some embodiments, the checkpoint inhibitor inhibits a protein selected from the group consisting of cytotoxic T-lymphocyte-associated antigen 4 (CTLA-4), programmed death 1 (PD-1), programmed death ligand-1 (PD-L1), LAG-3, T cell immunoglobulin mucin 3 (TIM-3), and killer immunoglobulin-like receptors (KIRs).

For example, in some embodiments, the checkpoint inhibitor is capable of binding to CTLA-4, PD-1, or PD-L1. In some embodiments, the checkpoint inhibitor interferes with the interaction (e.g., interferes with binding) between PD-1 and PD-L1.

In some embodiments, the checkpoint inhibitor is a small molecule.

In some embodiments, the checkpoint inhibitor is an antibody or antigen-binding fragment thereof, e.g., a monoclonal antibody. In some embodiments, the checkpoint inhibitor is a human or humanized antibody or antigen-binding fragment thereof. In some embodiments, the checkpoint inhibitor is a mouse antibody or antigen-binding fragment thereof.

In some embodiments, the checkpoint inhibitor is a CTLA-4 antibody. Non-limiting examples of CTLA-4 antibodies include BMS-986218, BMS-986249, ipilimumab, tremelimumab (formerly ticilimumab, CP-675,206), MK-1308, and REGN-4659. An additional example of a CTLA-4 antibody is 4F10-11, a mouse monoclonal antibody.

In some embodiments, the checkpoint inhibitor is a PD-1 antibody. Non-limiting examples of PD-1 antibodies include camrelizumab, cemiplumab, nivolumab, pembrolizumab, sintilimab, tislelizumab and toripalimab. An additional example of a PD-1 antibody is RMP1-14, a mouse monoclonal antibody.

In some embodiments, the checkpoint inhibitor is a PD-L1 antibody. Non-limiting examples of PD-L1 antibodies include atezolizumab, avelumab, and durvalumab.

In some embodiments, a combination of more than one checkpoint inhibitor is used. For example, in some embodiments, both a CTLA-4 inhibitor and a PD-1 or PD-L1 inhibitor is used.

Subjects

In some disclosed methods, a therapy (e.g., comprising a therapeutic agent) is administered to a subject. In some embodiments, the subject is a mammal, e.g., a human.

In some embodiments, the subject has received or is receiving another therapy. For example, in some embodiments, the subject has received or is receiving a radioimmunoconjugate. In some embodiments, the subject has received or is receiving a checkpoint inhibitor.

In some embodiments, the subject has cancer or is at risk of developing cancer. For example, the subject may have been diagnosed with cancer. The cancer may be a primary cancer or a metastatic cancer. Subjects may have any stage of cancer, e.g., stage I, stage II, stage III, or stage IV with or without lymph node involvement and with or without metastases. Provided compositions may prevent or reduce further growth of the cancer and/or otherwise ameliorate the cancer (e.g., prevent or reduce metastases). In some embodiments, the subject does not have cancer but has been determined to be at risk of developing cancer, e.g., because of the presence of one or more risk factors such as environmental exposure, presence of one or more genetic mutations or variants, family history, etc. In some embodiments, the subject has not been diagnosed with cancer.

In some embodiments, the cancer is a solid tumor.

In some embodiments, the solid tumor cancer is breast cancer, non-small cell lung cancer, small cell lung cancer, pancreatic cancer, head and neck cancer, prostate cancer, colorectal cancer, sarcoma, adrenocortical carcinoma, neuroendocrine cancer, Ewing's Sarcoma, multiple myeloma, or acute myeloid leukemia.

In some embodiments, the cancer is a non-solid (e.g., liquid (e.g., hematologic)) cancer.

Administration and Dosage

Effective and Lower Effective Doses

The present disclosure provides combination therapies in which the amounts of each therapeutic may or may not be, on their own, therapeutically effective. For example, provided are methods comprising administering a first therapy and a second therapy in amounts that together are effective to treat or ameliorate a disorder, e.g., cancer. In some embodiments, at least one of the first and second therapy is administered to the subject in a lower effective dose. In some embodiments, both the first and the second therapies are administered in lower effective doses.

In some embodiments, the first therapy comprises a radioimmunoconjugate and the second therapy comprises a checkpoint inhibitor.

In some embodiments, the first therapy comprises a checkpoint inhibitor and the second therapy comprises a radioimmunoconjugate.

In some embodiments, therapeutic combinations as disclosed herein are administered to a subject in a manner (e.g., dosing amount and timing) sufficient to cure or at least partially arrest the symptoms of the disorder and its complications. In the context of a single therapy (a "monotherapy"), an amount adequate to accomplish this purpose is defined as a "therapeutically effective amount," an amount of a compound sufficient to substantially improve at least one symptom associated with the disease or a medical condition. The "therapeutically effective amount" typically varies depending on the therapeutic. For known therapeutic agents, the relevant therapeutically effective amounts may be known to or readily determined by those of skill in the art.

For example, in the treatment of cancer, an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. For example, a treatment may be therapeutically effective if it causes a cancer to regress or to slow the cancer's growth.

The dosage regimen (e.g., amounts of each therapeutic, relative timing of therapies, etc.) that is effective for these uses may depend on the severity of the disease or condition and the weight and general state of the subject. For example, the therapeutically effective amount of a particular composition comprising a therapeutic agent applied to mammals (e.g., humans) can be determined by the ordinarily-skilled artisan with consideration of individual differences in age, weight, and the condition of the mammal. Because certain conjugates of the present disclosure exhibit an enhanced ability to target cancer cells and residualize, the dosage of these compounds can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agent. Therapeutically effective and/or optimal amounts can also be determined empirically by those of skill in the art. Thus, lower effective doses can also be determined by those of skill in the art.

Single or multiple administrations of a composition (e.g., a pharmaceutical composition comprising a therapeutic agent) can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

In the disclosed combination therapy methods, the first and second therapies may be administered sequentially or concurrently to a subject. For example, a first composition comprising a first therapeutic agent and a second composition comprising a second therapeutic agent may be administered sequentially or concurrently to a subject. Alternatively or additionally, a composition comprising a combination of a first therapeutic agent and a second therapeutic agent may be administered to the subject.

In some embodiments, the radioimmunoconjugate is administered in a single dose. In some embodiments, the radioimmunoconjugate is administered more than once. When the radioimmunoconjugate is administered more than once, the dose of each administration may be the same or different.

In some embodiments, the checkpoint inhibitor is administered in a single dose. In some embodiments, the checkpoint inhibitor is administered more than once, e.g., at least twice, at least three times, etc. In some embodiments, the checkpoint inhibitor is administered multiple times according to a regular or semi-regular schedule, e.g., once every approximately two weeks, once a week, twice a week, three times a week, or more than three times a week. When the checkpoint inhibitor is administered more than once, the dose of each administration may be the same or different. For example, the checkpoint inhibitor may be administered in an initial dose amount, and then subsequent dosages of the checkpoint inhibitor may be higher or lower than the initial dose amount.

In some embodiments, the first dose of the checkpoint inhibitor is administered at the same time as the first dose of the radioimmunoconjugate. In some embodiments, the first dose of the checkpoint inhibitor is administered before the first dose of radioimmunoconjugate. In some embodiments, the first dose of the checkpoint inhibitor is administered after the first dose of radioimmunoconjugate. In some embodiments, subsequent doses of the checkpoint inhibitor are administered.

In some embodiments, radioimmunoconjugates (or a composition thereof) and checkpoint inhibitors (or a composition thereof) are administered within 28 days (e.g., within 14, 7, 6, 5, 4, 3, 2, or 1 day(s)) of each other.

In some embodiments, radioimmunoconjugates (or a composition thereof) and checkpoint inhibitors (or a composition thereof) are administered within 90 days (e.g., within 80, 70, 60, 50, 40, 30, 20, 10, 5, 4, 3, 2, or 1 day(s)) of each other. In various embodiments the checkpoint inhibitor is administered at the same time as radioimmunoconjugate. In various embodiments, the checkpoint inhibitor is administered multiple times after the first administration of radioimmunoconjugate.

In some embodiments, compositions (such as compositions comprising radioimmunoconjugates) are administered for radiation treatment planning or diagnostic purposes. When administered for radiation treatment planning or diagnostic purposes, compositions may be administered to a subject in a diagnostically effective dose and/or an amount effective to determine the therapeutically effective dose. In some embodiments, a first dose of disclosed conjugate or a composition (e.g., pharmaceutical composition) thereof is administered in an amount effective for radiation treatment planning, followed administration of a combination therapy including a conjugate as disclosed herein and another therapeutic.

Pharmaceutical compositions comprising one or more agents (e.g., radioimmunoconjugates and/or checkpoint inhibitors) can be formulated for use in accordance with disclosed methods and systems in a variety of drug delivery systems. One or more physiologically acceptable excipients or carriers can also be included in the composition for proper formulation. Examples of suitable formulations are found in *Remington's Pharmaceutical Sciences*, Mack Publishing Company, Philadelphia, Pa., 17th ed., 1985. For a brief review of methods for drug delivery, see, e.g., Langer (*Science* 249:1527-1533, 1990).

Formulations

Pharmaceutical compositions may be formulated for parenteral, intranasal, topical, oral, or local administration, such as by a transdermal means, for prophylactic and/or therapeutic treatment. Pharmaceutical compositions can be administered parenterally (e.g., by intravenous, intramuscular, or subcutaneous injection), or by oral ingestion, or by topical application or intraarticular injection at areas affected by the vascular or cancer condition. Examples of additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Also specifically contemplated are sustained release administration, by such means as depot injections or erodible implants or components. Suitable compositions include compositions comprising include agents (e.g., compounds as disclosed herein) dissolved or suspended in an acceptable carrier, preferably an aqueous carrier, e.g., water, buffered water, saline, or PBS, among others, e.g., for parenteral administration. Compositions may contain pharmaceutically acceptable auxiliary substances to approximate physiological conditions, such as pH adjusting and buffering agents, tonicity adjusting agents, wetting agents, or detergents, among others. In some embodiments, compositions are formulated for oral delivery; for example, compositions may contain inert ingredients such as binders or fillers for the formulation of a unit dosage form, such as a tablet or a capsule. In some embodiments, compositions are formulated for local administration; for example, compositions may contain inert ingredients such as solvents or emulsifiers for the formulation of a cream, an ointment, a gel, a paste, or an eye drop.

Compositions may be sterilized, e.g., by conventional sterilization techniques, or sterile filtered. Aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 6 and 7, such as 6 to 6.5. In some embodiments, compositions in solid form are packaged in multiple single dose units, each containing a fixed amount of the above-mentioned agent or agents, such as in a sealed package of tablets or capsules. In some embodiments, compositions in solid form are packaged in a container for a flexible quantity, such as in a squeezable tube designed for a topically applicable cream or ointment.

Effects

In some embodiments, methods of the present disclosure result in a therapeutic effect. In some embodiments, the therapeutic effect comprises an immune response, for example, an immune response comprises an increase in T cells, e.g. CD8+ (e.g., IFNγ-producing CD8+ cells) and/or CD4+ cells. In some embodiments, the T cells comprise T cells specific for a tumor-associated antigen or tumor-specific antigen expressed on the cancer being treated or ameliorated. In some embodiments, the increase in T cells is observed in the tumor relative to the spleen.

In some embodiments, the step of administering results in at least 15%, at least 20%, at least 25%, at least 30%, at least 35%, at least 40%, at least 45%, at least 50%, at least 55%, at least 60%, at least 65%, or at least 70% of the total T cell population in a sample in the mammal being specific for the tumor-associated antigen or tumor-specific antigen. In some embodiments, the sample is a tumor sample.

In some embodiments, the therapeutic effect comprises a decrease in tumor volume, a stable tumor volume, or a reduced rate of increase in tumor volume. In some embodiments, the therapeutic effect comprises a decreased incidence of recurrence or metastasis.

Other Agents

In some embodiments, disclosed methods further include administering an antiproliferative agent, radiation sensitizer, or an immunoregulatory or immunomodulatory agent.

By "antiproliferative" or "antiproliferative agent," as used interchangeably herein, is meant any anticancer agent, including those antiproliferative agents listed in Table 2, any of which can be used in combination with a radioimmunoconjugate to treat a condition or disorder. Antiproliferative agents also include organo-platinum derivatives, naphtoquinone and benzoquinone derivatives, chrysophanic acid and anthroquinone derivatives thereof.

By "immunoregulatory agent" or "immunomodulatory agent," as used interchangeably herein, is meant any immuno-modulator, including those listed in Table 2, any of which can be used in combination with a radioimmunoconjugate.

As used herein, "radiation sensitizer" includes any agent that increases the sensitivity of cancer cells to radiation therapy. Radiation sensitizers may include, but are not limited to, 5-fluorouracil, analogs of platinum (e.g., cisplatin, carboplatin, oxaliplatin), gemcitabine, EGFR antagonists (e.g., cetuximab, gefitinib), farnesyltransferase inhibitors, COX-2 inhibitors, bFGF antagonists, and VEGF antagonists.

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | Miriplatin |
| | picoplatin | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | Edotecarin |
| | rebeccamycin analogue (Exelixis) | Cositecan |
| | BBR-3576 (Novuspharma) | Belotecan |
| | rubitecan (SuperGen) | hydroxycamptothecin (SN-38) |
| | irinotecan (CPT-11) | |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | Sabarubicin |
| | porfiromycin | Epirubicin |
| | mitoxantrone (novantrone) | mitoxantrone |
| | amonafide | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |

TABLE 2-continued

| | | |
|---|---|---|
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | β-alethine (Dovetail) |
| | p21 RAS vaccine (GemVax) | CLL therapy (Vasogen) |
| | MAGE-A3 (GSK) | Ipilimumab (BMS), |
| | nivolumab (BMS) | CM-10 (cCam Biotherapeutics) |
| | abatacept (BMS) | atezolizumab (Genentech) |
| | pembrolizumab (Merck) | |
| Hormonal and antihormonal agents | estrogens | dexamethasone |
| | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; | P-04 (Novogen) |
| | fluoxymesterone | 2-methoxyestradiol (EntreMed) |
| | methyltestosterone | arzoxifene (Eli Lilly) |
| | diethylstilbestrol | tamoxifen |
| | megestrol | toremofine |
| | bicalutamide | goserelin |
| | flutamide | Leuporelin |
| | nilutamide | bicalutamide |
| Photodynamic agents | talaporfin (Light Sciences) | Pd-bacteriopheophorbide (Yeda) |
| | Theralux (Theratechnologies) | Motexafin lutetium |
| | motexafin gadolinium (Pharmacyclics) | hypericin |
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |

TABLE 2-continued

| | |
|---|---|
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (lmClone) |
| | trastuzumab (Genentech) | Tyrphostins |
| | OSI-774 (Tarceva ™) | Gefitinib (Iressa) |
| | CI-1033 (Pfizer) | PTK787 (Novartis) |
| | SU11248 (Pharmacia) | EMD 72000 (Merck) |
| | RH3 (York Medical) | Emodin |
| | Genistein | Radicinol |
| | Radicinol | Vemurafenib (B-Raf enzyme |
| | Met-MAb (Roche) | inhibitor, Daiichi Sankyo) |
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | galarubicin (RNA synthesis inhibitor, Dong-A) |
| P54 (COX-2 inhibitor, Phytopharm) | tirapazamine (reducing agent, SRI |
| CapCell ™ (CYP450 stimulant, Bavarian Nordic) | International) |
| GCS-100 (gal3 antagonist, GlycoGenesys) | N-acetylcysteine (reducing agent, Zambon) |
| G17DT immunogen (gastrin inhibitor, Aphton) | R-flurbiprofen (NF-kappaB inhibitor, Encore) |
| efaproxiral (oxygenator, Allos Therapeutics) | 3CPA (NF-kappaB inhibitor, Active Biotech) |
| PI-88 (heparanase inhibitor, Progen) | seocalcitol (vitamin D receptor agonist, Leo) |
| tesmilifene (histamine antagonist, YM | 131-I-TM-601 (DNA antagonist, |
| BioSciences) | TransMolecular) |
| histamine (histamine H2 receptor agonist, Maxim) | eflornithine (ODC inhibitor, ILEX Oncology) |
| tiazofurin (IMPDH inhibitor, Ribapharm) | minodronic acid (osteoclast inhibitor, |
| cilengitide (integrin antagonist, Merck KGaA) | Yamanouchi) |
| SR-31747 (IL-1 antagonist, Sanofi-Synthelabo) | indisulam (p53 stimulant, Eisai) |
| CCI-779 (mTOR kinase inhibitor, Wyeth) | aplidine (PPT inhibitor, PharmaMar) |
| exisulind (PDE V inhibitor, Cell Pathways) | gemtuzumab (CD33 antibody, Wyeth Ayerst) |
| CP-461 (PDE V inhibitor, Cell Pathways) | PG2 (hematopoiesis enhancer, |
| AG-2037 (GARFT inhibitor, Pfizer) | Pharmagenesis) |
| WX-UK1 (plasminogen activator inhibitor, Wilex) | Immunol ™ (triclosan oral rinse, Endo) |
| PBI-1402 (PMN stimulant, ProMetic LifeSciences) | triacetyluridine (uridine prodrug, Wellstat) |
| bortezomib (proteasome inhibitor, Millennium) | SN-4071 (sarcoma agent, Signature |
| SRL-172 (T cell stimulant, SR Pharma) | BioScience) |
| TLK-286 (glutathione S transferase inhibitor, | TransMID-107 ™ (immunotoxin, KS Biomedix) |
| Telik) | PCK-3145 (apoptosis promotor, Procyon) |
| PT-100 (growth factor agonist, Point | doranidazole (apoptosis promotor, Pola) |
| Therapeutics) | CHS-828 (cytotoxic agent, Leo) |
| midostaurin (PKC inhibitor, Novartis) | trans-retinoic acid (differentiator, NIH) |
| bryostatin-1 (PKC stimulant, GPC Biotech) | MX6 (apoptosis promotor, MAXIA) |
| CDA-II (apoptosis promotor, Everlife) | apomine (apoptosis promotor, ILEX Oncology) |
| SDX-101 (apoptosis promotor, Salmedix) | urocidin (apoptosis promotor, Bioniche) |
| rituximab (CD20 antibody, Genentech | Ro-31-7453 (apoptosis promotor, La Roche) |
| carmustine | brostallicin (apoptosis promotor, Pharmacia) |
| Mitoxantrone | β-lapachone |
| Bleomycin | gelonin |
| Absinthin | cafestol |
| Chrysophanic acid | kahweol |
| Cesium oxides | caffeic acid |
| BRAF inhibitors, | Tyrphostin AG |
| PD-L1 inhibitors | PD-1 inhibitors |
| MEK inhibitors | CTLA-4 inhibitors |
| bevacizumab | sorafenib |
| angiogenesis inhibitors | |
| dabrafenib | |

EXAMPLES

Example 1. Single Agent Efficacy of Checkpoint Inhibitors in the CT-26 Syngeneic Model was Observed A single agent efficacy study of two checkpoint inhibitors (PD-1 and CTLA-4) was conducted in the CT-26 model, a murine colon carcinoma model. It is known that these carcinomas are partially sensitive to α-PD-1 mAbs and sensitive to α-CTLA-4 mAbs. Mice were injected i.p. with either 5 or 15 mg/kg i.p. of either the α-PD-1 mAb or the α-CTLA-4 mAb. The α-PD-1 mAb group was dosed twice a week for four weeks. The α-CTLA-4 mAb group was dosed only 3 times a day, 3 days apart. CTLA-4 treatment was more efficacious than PD-1 treatment, as expected for this model. In both treatment groups, 5 mg/kg appeared to be the most efficacious dose for impairing tumor growth. See FIG. 1. CD8+/CD4+ T cell recruitment following the different treatments is also measured using immunohistochemistry and flow cytometry techniques.

Figure 2:
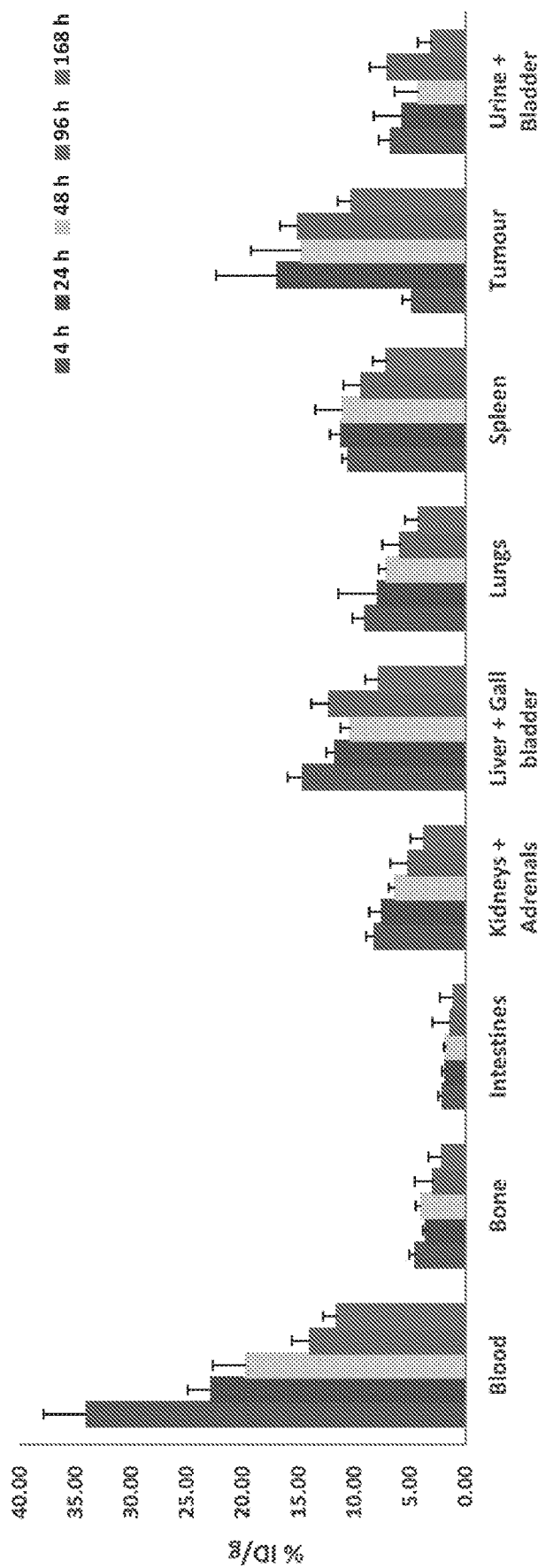
FIG. 2 illustrates [$^{177}Lu$]-FPI-1755 biodistribution in the CT-26 syngeneic mouse tumor model.

Example 2. [$^{177}$Lu]-FPI-1755 Biodistribution in the CT-26 Syngeneic Model MAB391, a murine monoclonal antibody against IGF-1R, was conjugated with FPI-1397 (a bifunctional chelate) and radiolabeled with Lu-177 using methods well known in the art to form [$^{177}$Lu]-FPI-1755. The ability of [$^{177}$Lu]-FPI-1755 to target antigen expressing mouse IGF-1R overexpressing tumors in vivo was demonstrated using the CT-26 syngeneic model. Tumor uptake was steady at 15-17% injected dose/g (ID/g) from 24-96 hours post injection. See FIG. 2.

Figure 3:
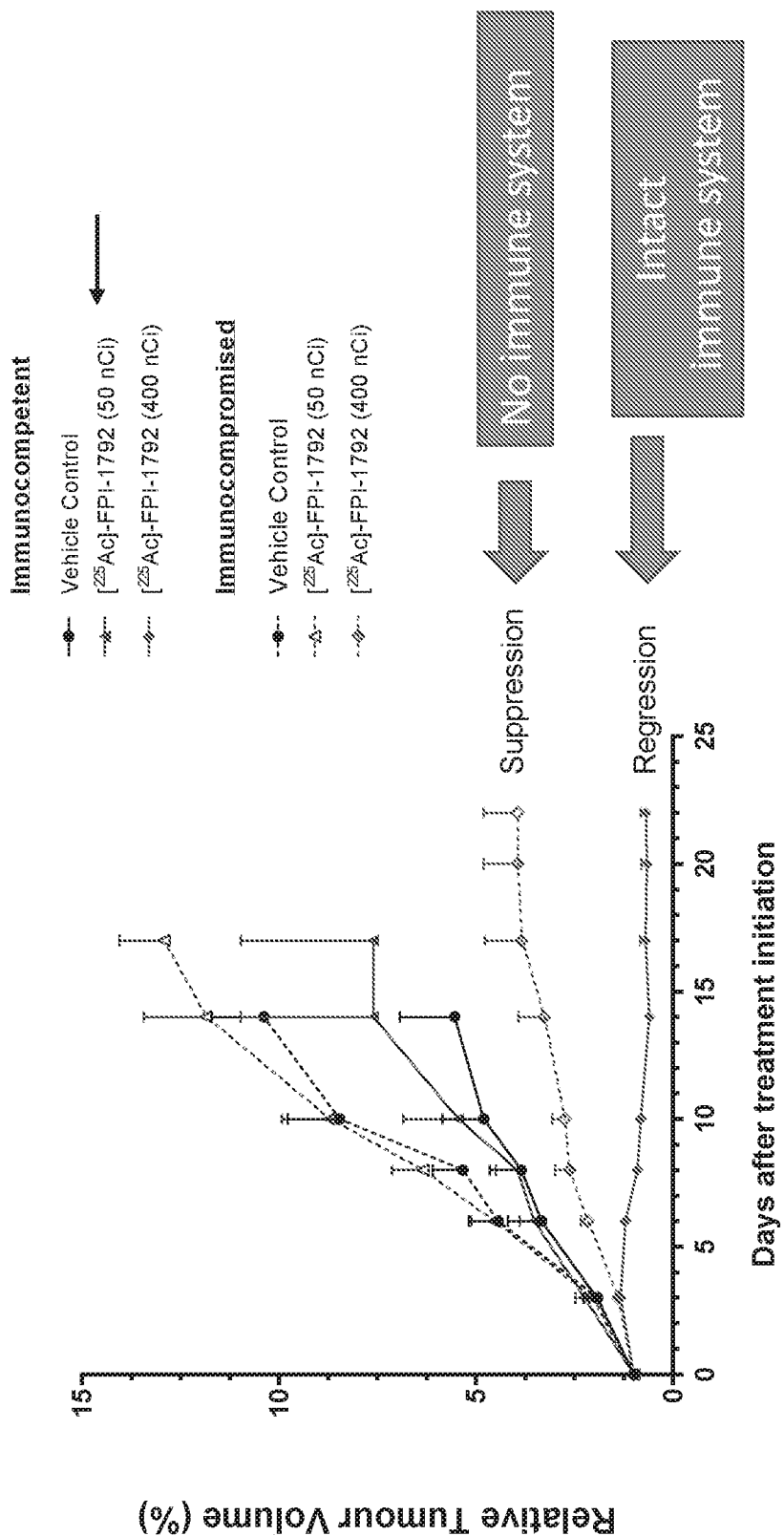
FIG. 3 illustrates the enhanced efficacy of [$^{225}Ac$]-FPI-1792 in immunocompetent mice vs. immunodeficient mice.

Example 3. Enhanced Efficacy of [$^{225}$Ac]-FPI-1792 in Immunocompetent vs. in Immunodeficient Mice MAB391, a murine monoclonal antibody against IGF-1R, was conjugated with FPI-1397 (a bifunctional chelate) and radiolabeled with [$^{225}$Ac] using standard techniques to form [$^{225}$Ac]-FPI-1792. An efficacy study of [$^{225}$Ac]-FPI-1792 in immunocompetent and in immunodeficient mice was conducted using a 400 nCi dose of [$^{225}$Ac]-FPI-1792. It was found that [$^{225}$Ac]-FPI-1792 had enhanced efficacy in reducing tumor volume in mice with an intact immune system relative to mice with no immune system. See FIG. 3.

Figure 4:
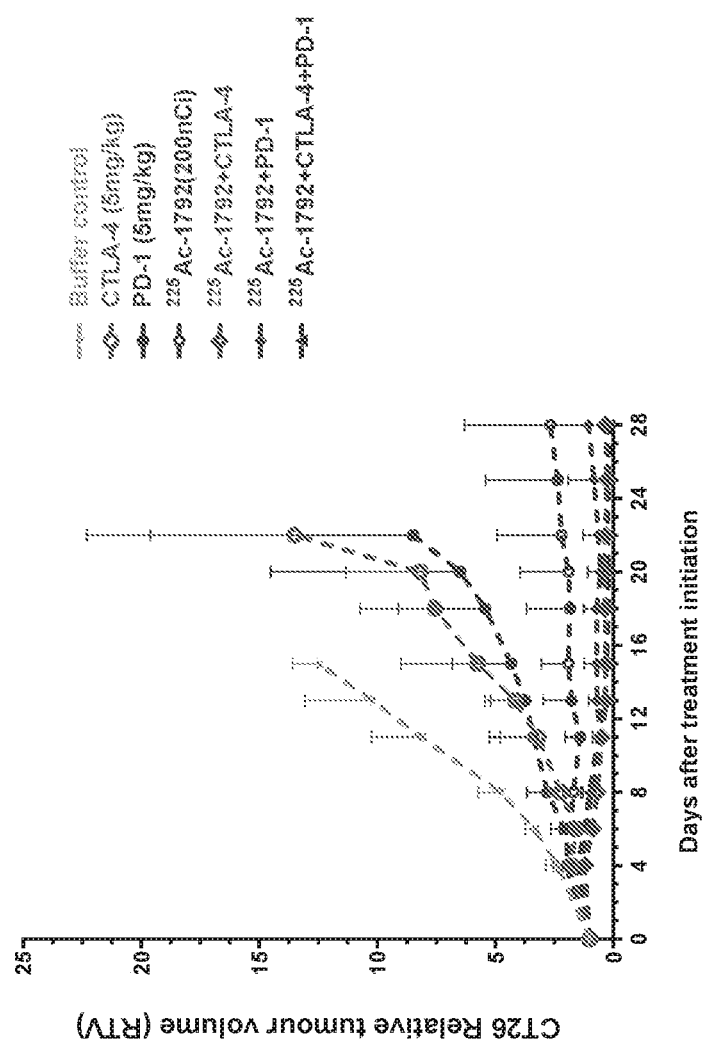
FIG. 4 illustrates synergy between [$^{225}Ac$]-FPI-1792 and α-CTLA-4/PD-1 treatment in the CT26 syngeneic mouse model.

Example 4. Synergy Between [$^{225}$Ac]-FPI-1792 and α-CTLA-4/PD-1 Treatment in the CT26 Syngeneic Mouse Model An in vivo synergy study was conducted to test the effect of [$^{225}$Ac]-FPI-1792 (as described in Example 3) and checkpoint inhibitors, α-CTLA-4 and α-PD-1 antibodies, on relative tumor volume in the CT26 mouse model. Mice treated either with the CTLA-4 inhibitor alone or the PD-1 inhibitor alone showed modest reductions in relative tumor volume when compared to the vehicle control groups. Mice treated with [$^{225}$Ac]-FPI-1792 demonstrated greater reductions in tumor volume relative to the vehicle control group or the groups administered CTLA-4 inhibitor or PD-1 inhibitor alone. However, when [$^{225}$Ac]-FPI-1792 was co-administered with ether CTLA-4 or PD-1 or both, a synergistic effect was seen—co-administration resulted in significantly smaller tumor volume when compared to treatment with [$^{225}$Ac]-FPI-1792, or when compared to treatment with the CTLA-4 inhibitor or the PD-1 inhibitor alone. See FIG. 4.

Figure 5:
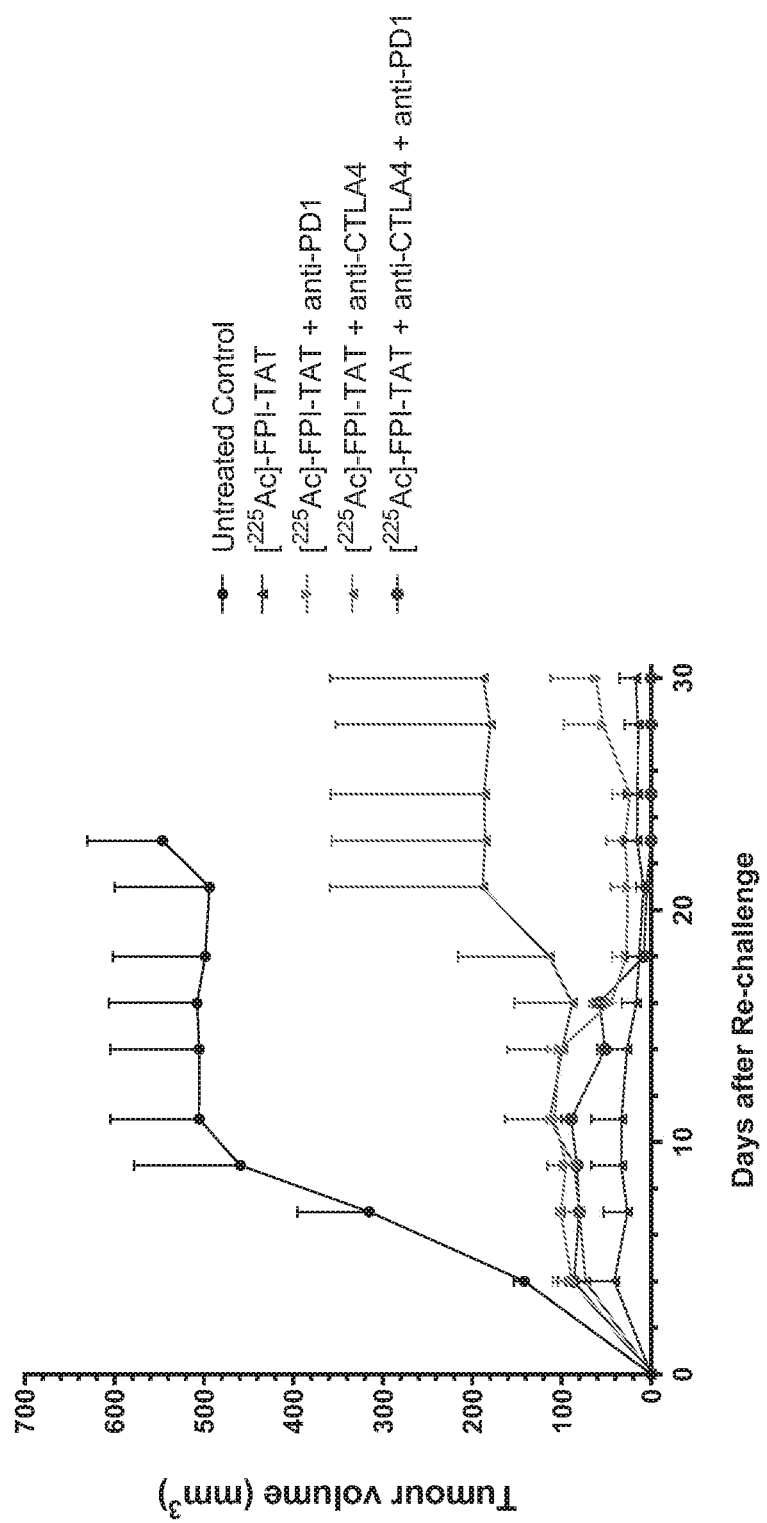
FIG. 5 illustrates the development of protective immunity in [$^{225}Ac$]-FPI-1792 ("[$^{225}Ac$]-FPI-TAT" in the graph labels) treated mice upon CT26 re-challenge.

Example 5. Development of Protective Immunity in [$^{225}$Ac]-FPI-1792 Retreated Mice Upon CT26 Re-Challenge A re-challenge experiment was conducted to test the development of protective immunity in [$^{225}$Ac]-FPI-1792 treated mice upon CT26 re-challenge. Mice had been previously treated with either [225Ac]-FPI-1792 alone or in combination with an α-CTLA-4 or α-PD-1 antibody. Naïve mice were used as controls. All mice previously treated with [$^{225}$Ac]-FPI-1792+/−an anti-CTLA-4 or anti-PD-1 antibody were protected from tumor challenge, suggesting development of protective T cell immunity. See FIG. 5.

Figure 6:
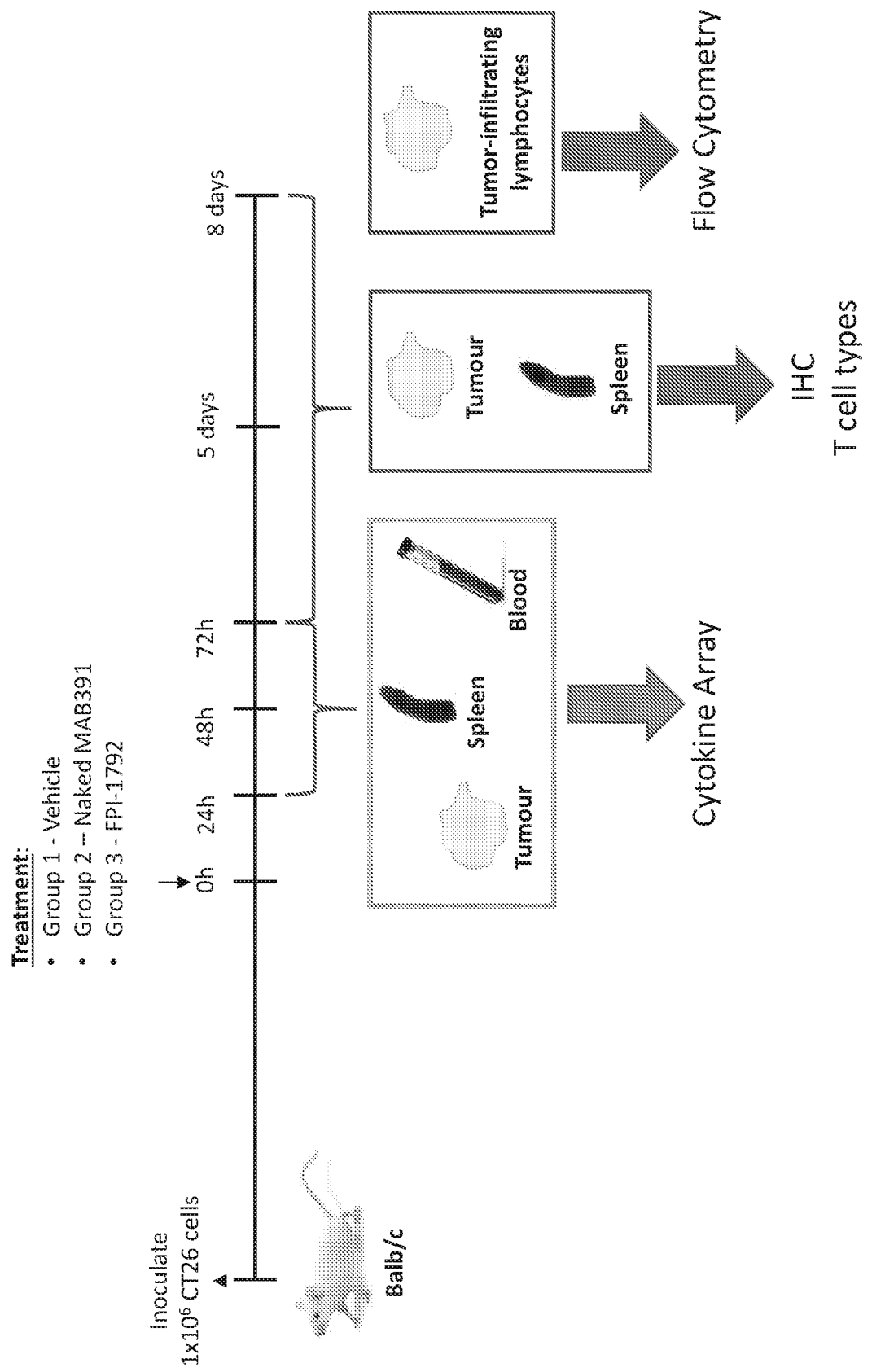
FIG. 6 illustrates cytokine response and T-cell recruitment after [$^{225}Ac$]-FPI-1792 treatment.

Example 6. Cytokine Response and T-Cell Recruitment After [$^{225}$Ac]-FPI-1792 Treatment Cytokine response and T-cell recruitment after [$^{225}$Ac]-FPI-1792 treatment is measured. Mice were inoculated with 1×10$^6$ CT26 cells. Mice were then treated with either [$^{225}$Ac]-FPI-1792, the unconjugated MAB391 antibody or vehicle. Samples from the tumor, spleen and blood plasma are analyzed for the presence of cytokines at 24, 48, or 72 hours. Additional samples are taken from the tumor and spleen at 72 hours, 5 days and 8 days for immunohistochemistry to assess the presence of different T-cell types. Finally, at 8 days, tumor-infiltrating lymphocytes are extracted, isolated and quantified using flow cytometry. See FIG. 6.

Figure 7:
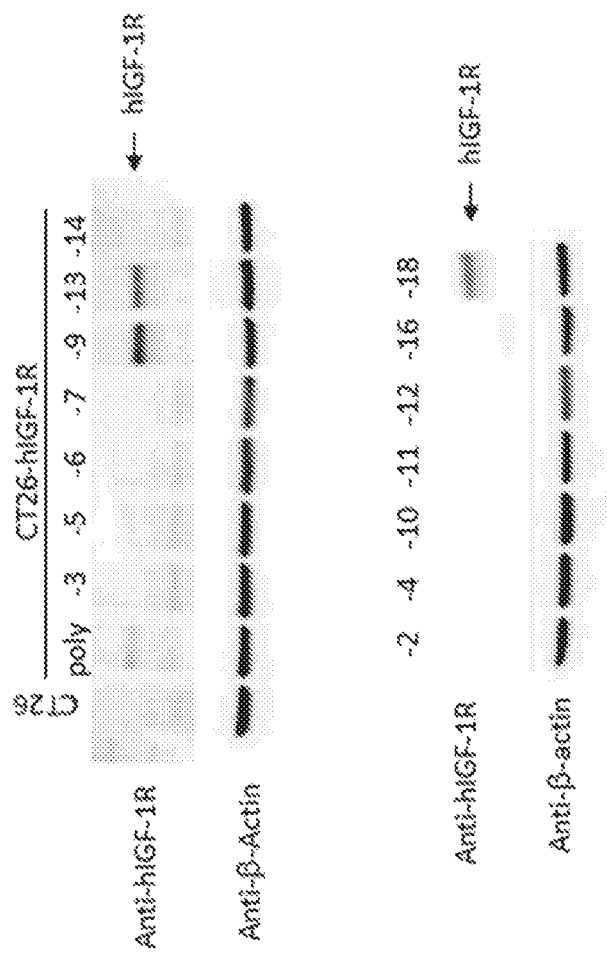
FIG. 7 illustrates "humanized" IGF-1R model development.

CT26 cells were stably transfected with human IGF-1R plasmid. Western blot analysis was conducted for the presence of hIGF-1R for the selection of hIGF-1R expressing clones. See FIG. 7. The best clones are chosen based on both in vitro and in vivo characteristics. The resulting cell lines will be used as an immunocompetent mouse model for testing [$^{225}$Ac]-FPI-1434 and other radioimmunoconjugates and additional synergies with immune checkpoint inhibitors.

Example 7. Combination Therapies Result in Increased Tumor-Associated Antigen-Specific CD8+ T Cells in Both the Spleen and Tumor Itself Ac-TAB-199 is a radioimmunoconjugate comprising human monoclonal IGF-1R antibody labeled with $^{225}$-Actinium. Combinations with Ac-TAB-199 and checkpoint inhibitors (α-PD-1, α-CTLA-4, or both α-PD-1 and α-CTLA-4) were tested in the CT26 syngeneic mouse model. Mice were re-challenged with CT26 cells at day 28 after initial tumor inoculation.

CD8+ and CD4+ T cell populations were assessed in both the spleen and the tumor after re-challenge. In mice treated with Ac-TAB-199 and checkpoint inhibitors, both the spleen and the tumor exhibited the presence of CD8+ T-cells. Importantly, an increase in the CD8+ T-cell frequency in the tumor, relative to controls, was observed. These results suggest that these combination treatments lead to improved levels of therapeutically effective CD8+ T cells.

Antigen-specific T-cells were detected and enumerated using an MHC class I tetramer assay. In this assay, MHC I molecules presenting an epitope specific to CT26 cells are labelled with biotin. In the presence of streptavidin, these MHC I molecules tetramerize. CD8+ T cells specific for the CD26 epitope are thereby labelled when their T-cell receptors bind to MHC I/CT26 epitope complexes within tetramers. Based on tetramer analysis, approximately 35%, 62%, and 75% of the CD8+ T cells were antigen-specific in mice treated with Ac-TAB-199/α-CTLA-4, Ac-TAB-199/α-PD-1, and Ac-TAB-199/α-CTLA-4/α-PD-1, respectively.

Equivalents/Other Embodiments

Those skilled in the art will recognize or be able to ascertain using no more than routine experimentation, many equivalents to the specific embodiments described herein. Such equivalents are intended to be encompassed by the following claims.

The invention claimed is:

1. A method of inducing an immune response to a tumor in a mammal, said method comprising:
   administering to the mammal Actinium-225 ($^{225}$Ac) targeted to said tumor,
   wherein said administering results in a therapeutically effective immune response which comprises at least 15% of T cells in a tumor sample being specific for a tumor-associated or tumor-specific antigen expressed on the tumor, and
   wherein said mammal also receives one or more checkpoint inhibitors.

* * * * *